(12) United States Patent
Whalley et al.

(10) Patent No.: US 9,522,123 B2
(45) Date of Patent: *Dec. 20, 2016

(54) USE OF ONE OR A COMBINATION OF PHYTO-CANNABINOIDS IN THE TREATMENT OF EPILEPSY

(71) Applicants: GW Pharma Limited, Salisbury (GB); Otsuka Pharmaceutical Co., Limited, Tokyo (JP)

(72) Inventors: Benjamin Whalley, Reading (GB); Gary Stephens, Reading (GB); Claire Williams, Reading (GB); Geoffrey Guy, Salisbury (GB); Stephen Wright, Salisbury (GB); Tetsuro Kikuchi, Osaka (JP)

(73) Assignees: GW Pharma Limited, Salisbury (GB); Otsuka Pharmaceutical Co., Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/579,061

(22) Filed: Dec. 22, 2014

(65) Prior Publication Data

US 2015/0335590 A1 Nov. 26, 2015

Related U.S. Application Data

(63) Continuation of application No. 13/380,305, filed as application No. PCT/GB2010/051066 on Jun. 29, 2010, now Pat. No. 9,066,920.

(30) Foreign Application Priority Data

Jul. 3, 2009 (GB) .................................. 0911580.9

(51) Int. Cl.
| | | |
|---|---|---|
| *A61K 31/06* | (2006.01) | |
| *A61K 31/352* | (2006.01) | |
| *A61K 31/05* | (2006.01) | |

(52) U.S. Cl.
CPC ............ *A61K 31/05* (2013.01); *A61K 31/352* (2013.01)

(58) Field of Classification Search
CPC .............................. A61K 31/05; A61K 31/352
USPC ................................................. 514/454, 729
See application file for complete search history.

(56) References Cited

U.S. PATENT DOCUMENTS

| | | | |
|---|---|---|---|
| 6,949,582 B1 | 9/2005 | Wallace | |
| 9,017,737 B2 | 4/2015 | Kikuchi et al. | |
| 9,023,322 B2 | 5/2015 | Van Damme et al. | |
| 9,066,920 B2* | 6/2015 | Whalley | A61K 31/352 |
| 9,125,859 B2 | 9/2015 | Whalley et al. | |
| 9,168,278 B2 | 10/2015 | Guy et al. | |
| 2006/0039959 A1 | 2/2006 | Wessling | |
| 2008/0119544 A1 | 5/2008 | Guy et al. | |
| 2009/0264063 A1 | 10/2009 | Tinsley et al. | |
| 2009/0306221 A1 | 12/2009 | Guy et al. | |
| 2010/0239693 A1 | 9/2010 | Guy et al. | |
| 2010/0317729 A1 | 12/2010 | Guy et al. | |
| 2011/0038958 A1 | 2/2011 | Kikuchi et al. | |
| 2011/0082195 A1 | 4/2011 | Guy et al. | |
| 2012/0004251 A1 | 1/2012 | Whalley et al. | |
| 2012/0165402 A1 | 6/2012 | Whalley et al. | |
| 2012/0270845 A1 | 10/2012 | Bannister et al. | |
| 2013/0245110 A1 | 9/2013 | Guy et al. | |
| 2014/0155456 A9 | 6/2014 | Whalley et al. | |
| 2014/0243405 A1 | 8/2014 | Whalley et al. | |
| 2014/0335208 A1 | 11/2014 | Cawthorne et al. | |
| 2015/0181924 A1 | 7/2015 | Llamas | |
| 2015/0320698 A1 | 11/2015 | Whalley et al. | |
| 2015/0359755 A1 | 12/2015 | Guy et al. | |
| 2015/0359756 A1 | 12/2015 | Guy et al. | |
| 2016/0166514 A1 | 6/2016 | Guy et al. | |
| 2016/0166515 A1 | 6/2016 | Guy et al. | |

FOREIGN PATENT DOCUMENTS

| | | |
|---|---|---|
| AU | 2012314129 | 3/2015 |
| GB | 2 384 707 A | 8/2003 |
| GB | 2 434 097 A | 7/2007 |
| GB | 2 434 312 A | 7/2007 |
| GB | 2 450 753 A | 1/2009 |
| GB | 2 456 183 A | 7/2009 |
| GB | 2 471 523 A | 1/2011 |
| GB | 2 478 595 A | 9/2011 |
| GB | 2 479 153 A | 10/2011 |
| GB | 2 471 565 B | 7/2012 |
| GB | 2 478 072 B | 12/2012 |
| GB | 2 478 074 B | 12/2012 |
| GB | 2 492 487 A | 1/2013 |
| GB | 1410771.8 | 2/2015 |

(Continued)

OTHER PUBLICATIONS

Statement of Opposition for EP10734541.5 mailed Dec. 5, 2014.
Third Party Observations for Application No. EP11712658.1 mailed Nov. 22, 2013.
Combined Search and Examination Report mailed Mar. 25, 2011 for Application No. GB1100043.7.
Examination Report mailed Mar. 18, 2014 for Application No. GB1100043.7.
Combined Search and Examination Report mailed Jan. 4, 2012 for Application No. GB1116789.7.
Examination Report mailed Feb. 29, 2012 for Application No. GB1121919.3.
Combined Search and Examination Report mailed Sep. 5, 2014 for Application No. GB1414813.4.
International Search Report and Written Opinion mailed Dec. 13, 2010 for Application No. PCT/GB2010/051066.
International Preliminary Report on Patentability mailed Jun. 9, 2011 for Application No. PCT/GB2010/051066.

(Continued)

*Primary Examiner* — Raymond Henley, III
(74) *Attorney, Agent, or Firm* — Wolf, Greenfield & Sacks, P.C.

(57) ABSTRACT

This invention relates to the use of one or more cannabinoids in the treatment of epilepsy and more particularly to the use of one or a combination of cannabinoids in the treatment of generalized or partial seizure. In one embodiment it relates to the use of the cannabinoid THCV, as a pure or isolated compound, or as a plant extract in which significant amounts of any THC naturally present has been selectively removed. In another embodiment the phytocannabinoid is CBD.

13 Claims, 21 Drawing Sheets

(56) References Cited

FOREIGN PATENT DOCUMENTS

| | | |
|---|---|---|
| GB | 1506550.1 | 2/2016 |
| WO | WO 02/064109 A2 | 8/2002 |
| WO | WO 03/099302 A1 | 12/2003 |
| WO | WO 2004/016246 A1 | 2/2004 |
| WO | WO 2004/016277 A2 | 2/2004 |
| WO | WO 2006/054057 A2 | 5/2006 |
| WO | WO 2006/133941 A2 | 12/2006 |
| WO | WO 2007/083098 A1 | 7/2007 |
| WO | WO 2007/138322 A1 | 12/2007 |
| WO | WO 2008/146006 A1 | 12/2008 |
| WO | WO 2009/007697 A1 | 1/2009 |
| WO | WO 2011/001169 A1 | 1/2011 |
| WO | WO 2011/121351 A1 | 10/2011 |
| WO | WO 2012/093255 A1 | 7/2012 |
| WO | WO 2013/032351 A1 | 3/2013 |
| WO | PCT/GB2015/051775 | 8/2015 |
| WO | PCT/GB2015/051776 | 8/2015 |
| WO | WO 2015/142501 A1 | 9/2015 |
| WO | WO 2015/184127 A2 | 12/2015 |

OTHER PUBLICATIONS

International Search Report and Written Opinion mailed May 30, 2011 for Application No. PCT/GB2011/050649.
International Search Report mailed Feb. 24, 2012 for Application No. PCT/GB2012/050002.
International Search Report and Written Opinion mailed Nov. 16, 2012 for Application No. PCT/GB2012/052284.
International Preliminary Report on Patentability mailed Dec. 12, 2013 for Application No. PCT/GB2012/052284.
[No Author Listed] Estimating the Maximum Safe Starting Dose in Initial Clinical Trials for Therapeutics in Adult Healthy Volunteers. FDA Guidance for Industry, Jul. 2005.
Alger, Not too excited? Thank your endocannabinoids. Neuron. Aug. 17, 2006;51(4):393-5.
Ames et al., Anticonvulsant effect of cannabidiol. S Afr Med J. Jan. 4, 1986;69(1):14.
Arain et al., Pregabalin in the management of partial epilepsy. Neuropsychiatr Dis Treat. 2009;5:407-13. Epub Aug. 20, 2009.
Avoli et al., Cellular and molecular mechanisms of epilepsy in the human brain. Prog Neurobiol. Oct. 2005;77(3):166-200.
Bancaud et al., Proposal for Revised Clinical and Electroencephalographic Classification of Epileptic Seizures. Epilepsia. Aug. 1981;22(4):489-501.
Bhatt et al., Indigenous plants in traditional healthcare system in Kedarnath valley of western Himalaya. Indian J Tradit Knowl. Apr. 2008;7(2):300-10.
Bhattacharyya et al., Modulation of mediotemporal and ventrostriatal function in humans by Delta9-tetrahydrocannabinol: a neural basis for the effects of Cannabis sativa on learning and psychosis. Arch Gen Psychiatry. Apr. 2009;66(4):442-51. doi:10.1001/archgenpsychiatry.2009.17.
Bostanci et al., The effects of octanol on penicillin induced epileptiform activity in rats: an in vivo study. Epilepsy Res. Oct. 2006;71(2-3):188-94. Epub Jul. 27, 2006.
Brust et al., Marijuana use and the risk of new onset seizures. Trans Am Clin Climatol Assoc. 1992;103:176-81.
Carlini et al., Hypnotic and antiepileptic effects of cannabidiol. J Clin Pharmacol. Aug.-Sep. 1981;21(8-9 Suppl):417S-427S. Medline abstract only.
Consroe et al., Anticonvulsant interaction of cannabidiol and ethosuximide in rats. J Pharm Pharmacol. Aug. 1977;29(8):500-1.
Consroe et al., Anticonvulsant nature of marihuana smoking. JAMA. Oct. 20, 1975;234(3):306-7.
Consroe et al., Cannabidiol—antiepileptic drug comparisons and interactions in experimentally induced seizures in rats. J Pharmacol Exp Ther. Apr. 1977;201(1):26-32.
Consroe et al., Effects of cannabidiol on behavioral seizures caused by convulsant drugs or current in mice. Eur J Pharmacol. Sep. 24, 1982;83(3-4):293-8.
Cortesi et al., Potential therapeutical effects of cannabidiol in children with pharmacoresistant epilepsy. Med Hypotheses. 2007;68(4):920-1. Epub Nov. 16, 2006.
Cunha et al., Chronic administration of cannabidiol to healthy volunteers and epileptic patients. Pharmacology. 1980;21(3):175-85.
Czapinski et al., Randomized 36-month comparative study of valproic acid (VPA), phenytoin (PHT), phenobarbital (PB) and carbamazepine (CBZ) efficacy in patients with newly diagnosed epilepsy with partial complex seizures. J Neurolog Sci. Sep. 1997;150:S162. Abstract only. 2 pages.
Davis et al., A predominant role for inhibition of the adenylate cyclase/protein kinase A pathway in ERK activation by cannabinoid receptor 1 in N1E-115 neuroblastoma cells. J Biol Chem. Dec. 5, 2003;278(49):48973-80. Epub Sep. 29, 2003.
Davis et al., Antiepileptic action of marijuana-active substances. Federation Proceedings. 1949;8:284-5.
Deshpande et al., Cannabinoid CB1 receptor antagonists cause status epilepticus-like activity in the hippocampal neuronal culture model of acquired epilepsy. Neurosci Lett. Jan. 2007;411(1):11-6. Epub Nov. 15, 2006.
Engel, Report of the ILAE classification core group. Epilepsia. Sep. 2006;47(9):1558-68.
Ferdinand et al., Cannabis—psychosis pathway independent of other types of psychopathology. Schizophr Res. Nov. 15, 2005;79(2-3):289-95. Epub Aug. 25, 2005.
Fisher et al., The impact of epilepsy from the patient's perspective I. Descriptions and subjective perceptions. Epilepsy Res. Aug. 2000;41(1):39-51.
Gabor et al., Lorazepam versus phenobarbital : Candidates for drug of choice for treatment of status epilepticus. J Epilepsy. Jan. 1990;3(1):3-6.
Gastaut, Clinical and electroencephalographical classification of epileptic seizures. Epilepsia. Mar. 1970;11(1):102-13.
Gross et al., Marijuana use and epilepsy: prevalence in patients of a tertiary care epilepsy center. Neurology. Jun. 8, 2004;62(11):2095-7.
Hill et al., $\Delta^9$-Tetrahydrocannabivarin suppresses in vitro epileptiform and in vivo seizure activity in adult rats. Epilepsia. Aug. 2010;51(8):1522-32. doi: 10.1111/j.1528-1167.2010.02523.x. Epub Feb. 26, 2010.
Iuvone et al., Neuroprotective effect of cannabidiol, a non-psychoactive component from Cannabis sativa, on beta-amyloid-induced toxicity in PC12 cells. J Neurochem. Apr. 2004;89(1):134-41.
Jeavons et al., Sodium valproate in treatment of epilepsy. Br Med J. Jun. 15, 1974;2(5919):584-6.
Jones et al., Cannabidiol displays antiepileptiform and antiseizure properties in vitro and in vivo. J Pharmacol Exp Ther. Feb. 2010;332(2):569-77. doi: 10.1124/jpet.109.159145. Epub Nov. 11, 2009.
Joy et al., Marijuana and Medicine. Assessing the Science Base. National Academy Press. Washington D.C. 1999. 170 pages.
Karler et al., The cannabinoids as potential antiepileptics. J Clin Pharmacol. Aug.-Sep. 1981;21(8-9 Suppl):437S-447S.
Khan et al., Khazaain-al-Advia, vol. I. 1911: 889. Urdu. Exhibit 3.
Khan et al., Khazaain-al-Advia, vol. I. 1911: 889. Urdu. Exhibit 4.
Khan et al., Muheet-e-Azam, vol. II. 1887: 147. Persian. Exhibit 1.
Long et al., The pharmacological actions of cannabidiol. Drugs of the Future. Jul. 2005;30(7):747-53.
Lutz, On-demand activation of the endocannabinoid system in the control of neuronal excitability and epileptiform seizures. Biochem Pharmacol. Nov. 1, 2004;68(9):1691-8.
Mackie, Cannabinoid receptors as therapeutic targets. Annu Rev Pharmacol Toxicol. 2006;46:101-22.
Majoosi, et al. Kaamil-al-Sena'ah, Part II, Central Council for Research in Unani Medicine. 2005:116. Arabic. Exhibit 2.
McCormick et al., On the cellular and network bases of epileptic seizures. Annu Rev Physiol. 2001;63:815-46.
Merlis, Proposal for an international classification of the epilepsies. Epilepsia. Mar. 1970;11(1):114-9.
Ng et al., Illicit drug use and the risk of new-onset seizures. Am J Epidemiol. Jul. 1990;132(1):47-57.

(56) References Cited

OTHER PUBLICATIONS

Obay et al., Antiepileptic effects of ghrelin on pentylenetetrazole-induced seizures in rats. Peptides. Jun. 2007;28(6):1214-9. Epub Apr. 19, 2007.
Pereira et al., Study pharmacologic of the GABAergic and glutamatergic drugs on seizures and status epilepticus induced by pilocarpine in adult Wistar rats. Neurosci Lett. Jun. 4, 2007;419(3):253-7. Epub Apr. 13, 2007.
Pertwee, Cannabinoid receptor ligands: clinical and neuropharmacological considerations, relevant to future drug discovery and development. Expert Opin Investig Drugs. Jul. 2000;9(7):1553-71.
Rauca et al., The role of superoxide dismutase and alpha-tocopherol in the development of seizures and kindling induced by pentylenetetrazol—influence of the radical scavenger alpha-phenyl-N-tert-butyl nitrone. Brain Res. May 29, 2004;1009(1-2):203-12.
Resstel et al., 5-HT1A receptors are involved in the cannabidiol-induced attenuation of behavioural and cardiovascular responses to acute restraint stress in rats. Br J Pharmacol. Jan. 2009;156(1):181-8.
Sander, The epidemiology of epilepsy revisited. Curr Opin Neurol. Apr. 2003;16(2):165-70.
Scuderi et al., Cannabidiol in medicine: a review of its therapeutic potential in CNS disorders. Phytother Res. May 2009;23(5):597-602.
Swann et al., The effects of seizures on the connectivity and circuitry of the developing brain. Ment Retard Dev Disabil Res Rev. 2004;10(2):96-100.
Thomas et al., Evidence that the plant cannabinoid Delta9-tetrahydrocannabivarin is a cannabinoid CB1 and CB2 receptor antagonist. Br J Pharmacol. Dec. 2005;146(7):917-26.
Trembly et al., Double-blind clinical study of cannabidiol as a secondary anticonvulsant Marijuana '90 International Conference on Cannabis and Cannabinoids. Kolymbari, Crete. Jul. 8-11, 1990.
Usami et al., Synthesis and pharmacological evaluation in mice of halogenated cannabidiol derivatives. Chem Pharm Bull (Tokyo). Nov. 1999;47(11):1641-5.
Wahle et al., Development of tolerance to the anticonvulsant effect of valproate but not to ethosuximide in a rat model of absence epilepsy. Eur J Pharma. May 1990;181(1-2):1-8.
Wallace et al., Assessment of the role of CB1 receptors in cannabinoid anticonvulsant effects. Eur J Pharmacol. Sep. 28, 2001;428(1):51-7.
Weston et al., Tetrahydrocannabivarin exhibits anticonvulsant effects in a piriform cortical brain slice model of epileptiform activity. Pro British Pharm Soc 75th Anniv Meeting. Dec. 31, 2006 Found on: http://www.pA2online.org/abstract/abstract.jsp?abid=28533. Abstract Only. 1 Page.
Wingerchuk, Cannabis for medical purposes: cultivating science, weeding out the fiction. Lancet. Jul. 24-30, 2004;364(9431):315-6.
Yuriev, Endogenic cannabinoid system is a new perspective object of pharmacotherapeutic effect to disease of nervous system, Ukrainsky Methodichny Chasopis, 2005; 6(50): 21-9.
Zuardi et al., Cannabidiol, a Cannabis sativa constituent, as an antipsychotic drug. Braz J Med Biol Res. Apr. 2006;39(4):421-9. Epub Apr. 3, 2006.
[No Author Listed] Orphan Drug Designation Granted for Epidiolex in Dravet syndrome by the FDA—Seven Expanded Access INDs granted by FDA to US physicians to treat with Epidiolex 125 children suffering from intractable epilepsy syndromes. GW Pharmaceuticals Press Release dated Nov. 14, 2013.
[No Author Listed] Cannabinoid. Wikipedia. Retrieved on Jul. 9, 2015 from https://en.wikipedia.org/wiki/Cannabinoid.
[No Author Listed] GW Pharmaceuticals Announces Epidiolex Receives Fast Track Designation from FDA for the Treatment of Dravet Syndrome. GW Pharmaceuticals Press Release dated Jun. 6, 2014.
[No Author Listed] GW Pharmaceuticals Announces Physician Reports of Epidiolex Treatment Effect in Children and Young Adults with Treatment-resistant epilepsy from Physician-Led Expanded Access Treatment Program. GW Pharmaceuticals Press Release dated Jun. 17, 2014.
Consroe et al., Anticonvulsant drug antagonism of delta9tetrahydrocannabinol-induced seizures in rabbits. Res Commun Chem Pathol Pharmacol. Jan. 1977;16(1):1-13.
Dravet, The core Dravet syndrome phenotype. Epilepsia. Apr. 2011;52 Suppl 2:3-9. doi: 10.1111/j.1528-1167.2011.02994.x.
Eadie, Shortcomings in the current treatment of epilepsy. Expert Rev Neurother. Dec. 2012;12(12):1419-27. doi: 10.1586/ern.12.129.
Gresham et al., Treating Lennox-Gastaut syndrome in epileptic pediatric patients with thirdgeneration rufinamide. Neuropsychiatr Dis Treat. Oct. 5, 2010;6:639-45. doi: 10.2147/NDT.S6465.
Kramer et al., Febrile infection-related epilepsy syndrome (FIRES): pathogenesis, treatment, and outcome: a multicenter study on 77 children. Epilepsia. Nov. 2011;52(11):1956-65.doi:10.1111/j.1528-1167.2011.03250.x. Epub Aug. 29, 2011.
Kwan et al., Definition of drug resistant epilepsy: consensus proposal by the ad hoc Task Force of the ILAE Commission on Therapeutic Strategies. Epilepsia. Jun. 2010;51(6):1069-77.doi:10.1111/j.1528-1167.2009.02397.x. Epub Nov. 3, 2009. Erratum in: Epilepsia. Sep. 2010;51(9):1922.
Maa et al., The case for medical marijuana in epilepsy. Epilepsia. Jun. 2014;55(6):783-6. doi:10.1111/epi.12610. Epub May 22, 2014.
Mechoulam et al., Toward drugs derived from cannabis. Naturwissenschaften. Apr. 1978;65(4):174-9.
Porter et al., Report of a parent survey of cannabidiol-enriched cannabis use in pediatric treatment-resistant epilepsy. Epilepsy Behav. Dec. 2013;29(3):574-7. doi:10.1016/j.yebeh.2013.08.037.
Press et al., Parental reporting of response to oral cannabis extracts for treatment of refractory epilepsy. Epilepsy Behav. Apr. 2015;45:49-52. doi: 10.1016/j.yebeh.2015.02.043. Epub Apr. 3, 2015.
Stott et al., Cannabinoids for the pharmaceutical industry. Euphytica. 2004;140:83-93.
Thurman et al., Standards for epidemiologic studies and surveillance of epilepsy. Epilepsia. Sep. 2011;52 Suppl 7:2-26. doi:10.1111/j.1528-1167.2011.03121.x.
U.S. Appl. No. 14/851,378, filed Sep. 11, 2015, Pending.

* cited by examiner

Figure 16 A-B
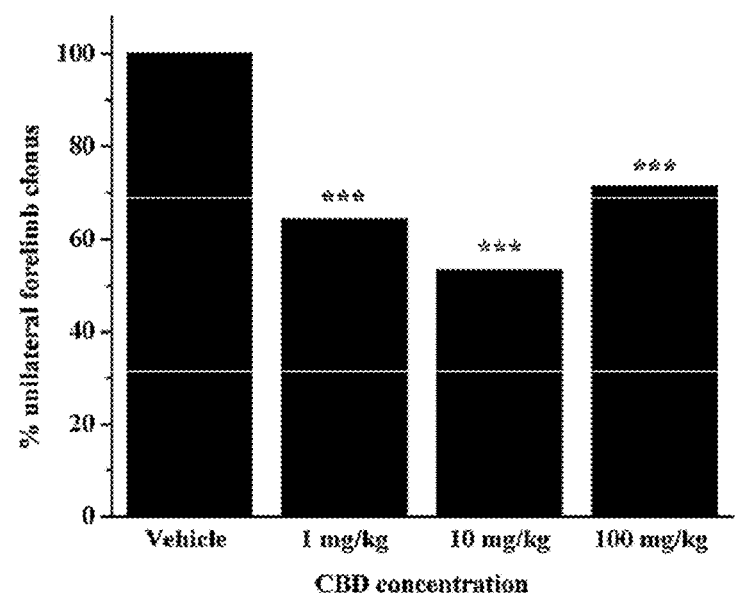
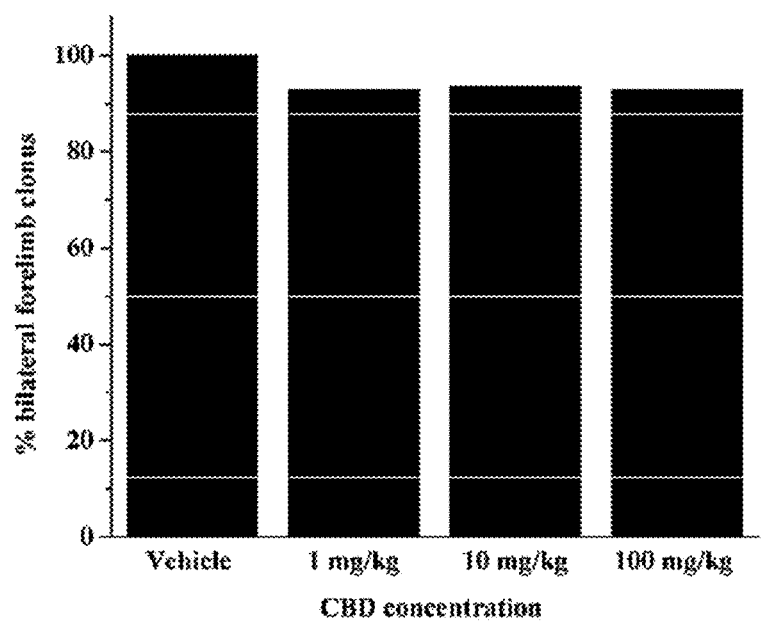

Figure 16 C-D
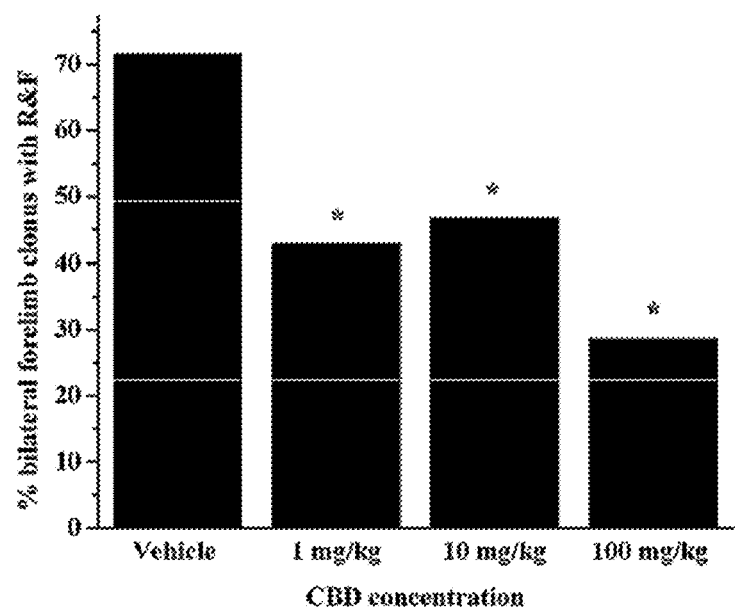
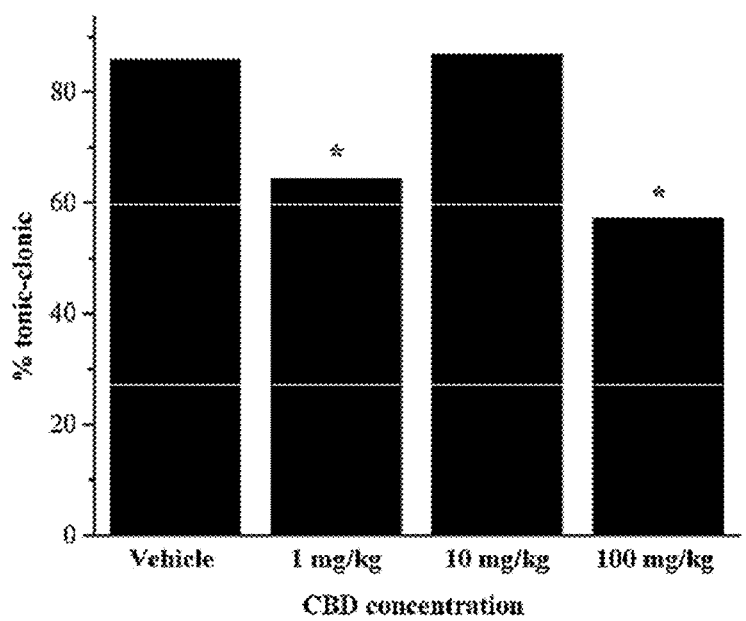

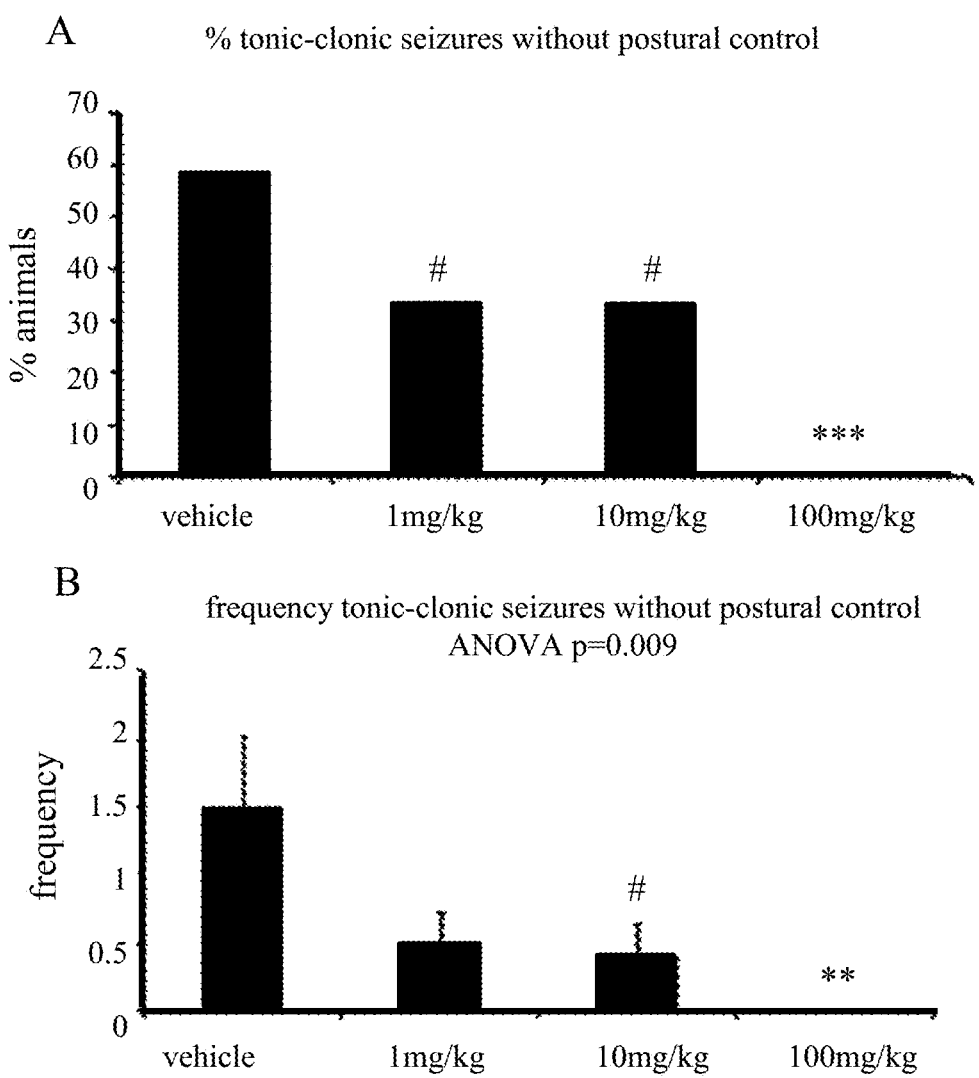
Figure 19 A-B

Figure 20 A-C
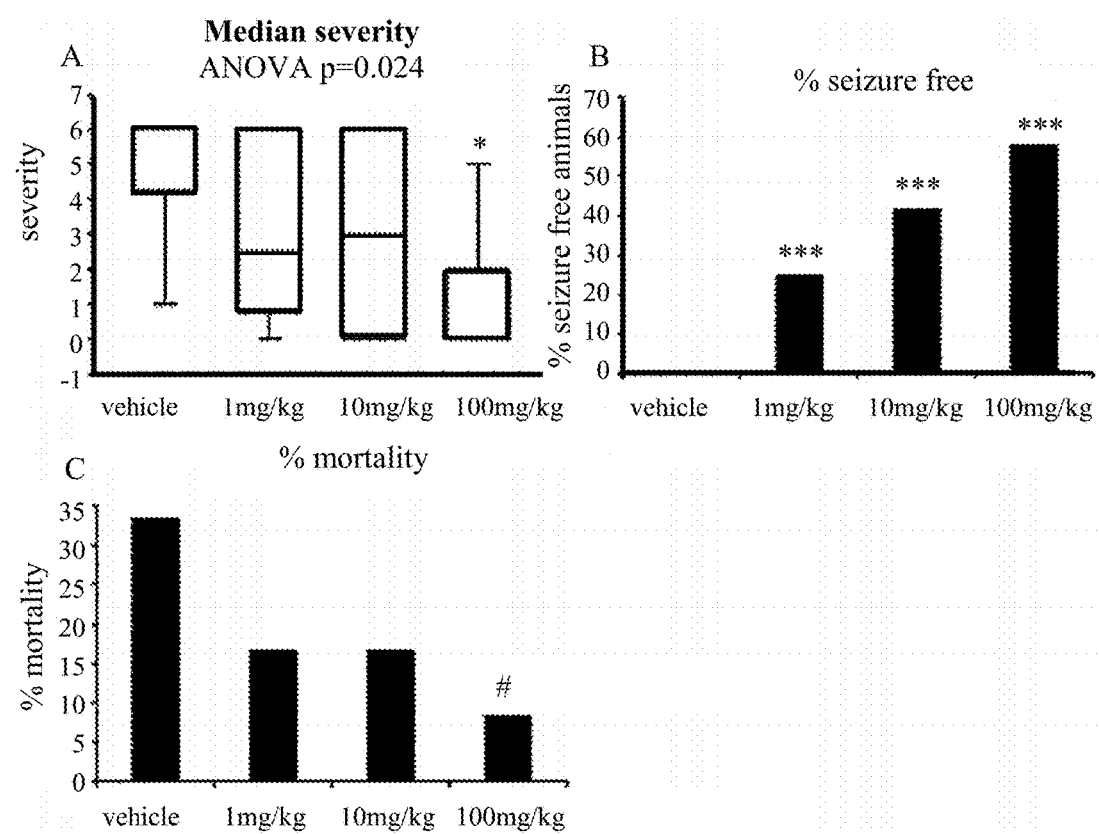

USE OF ONE OR A COMBINATION OF PHYTO-CANNABINOIDS IN THE TREATMENT OF EPILEPSY

RELATED APPLICATIONS

This application is a continuation of U.S. patent application Ser. No. 13/380,305, now U.S. Pat. No. 9,066,920, filed Mar. 19, 2012, which application is a national stage filing under 35 U.S.C. §371 of international application PCT/GB2010/051066, filed Jun. 29, 2010, which was published under PCT Article 21(2) in English, the entire contents of which are incorporated herein by reference.

This invention relates to the use of one or a combination of phyto-cannabinoids in the treatment of epilepsy and more particularly to the use of tetrahydrocannabivarin (THCV) in the treatment of generalized seizure and/or cannabidiol (CBD) in generalized seizure and/or partial seizures (in contrast to temporal lobe seizures).

BACKGROUND

Epilepsy is a chronic neurological disorder presenting a wide spectrum of diseases that affects approximately 50 million people worldwide (Sander, 2003). Advances in the understanding of the body's internal 'endocannabinoid' system have lead to the suggestion that some *cannabis*-based medicines may have the potential to treat this disorder of hyperexcitability in the central nervous system (Mackie, 2006, Wingerchuk, 2004, Alger, 2006).

*Cannabis* has been ascribed both pro-convulsant (Brust et al., 1992) and anti-convulsant effects. Therefore, it remains to be determined whether cannabinoids represent a yet to be unmasked therapeutic anticonvulsant or, conversely, a potential risk factor to recreational and medicinal users of *cannabis* (Ferdinand et al., 2005).

In 1975 Consroe et al. described the case of young man whose standard treatment (phenobarbital and phenytoin), didn't control his seizures. When he began to smoke *cannabis* socially he had no seizures. However when he took only *cannabis* the seizures returned. They concluded that 'marihuana may possess an anti-convulsant effect in human epilepsy'.

A study by Ng (1990) involved a larger population of 308 epileptic patients who had been admitted to hospital after their first seizure. They were compared to a control population of 294 patients who had not had seizures, and it was found that using *cannabis* seemed to reduce the likelihood of having a seizure. However this study was criticized in an Institute of Medicine report (1999) which claimed it was 'weak', as 'the study did not include measures of health status prior to hospital admissions and differences in their health status might have influenced their drug use' rather than the other way round.

In WO02/064109 reference is made to the anti epileptic effects of the cannabinoid cannabidiol (CBD).

WO 2006/054057 makes reference to the potential use of THCV to treat epilepsy amongst a range of diseases.

WO2009/007697 discloses formulations containing THCV and CBD.

Three controlled trials have investigated the anti-epilepsy potential of cannabidiol. In each, cannabidiol was given in oral form to sufferers of generalised grand mail or focal seizures.

Cunha et al (1980) reported a study on 16 grand mal patients who were not doing well on conventional medication. They received their regular medication and either 200-300 mg of cannabidiol or a placebo. Of the patients who received CBD, 3 showed complete improvement, 2 partial, 2 minor, while 1 remained unchanged. The only unwanted effect was mild sedation. Of the patients who received the placebo, 1 improved and 7 remained unchanged.

Ames (1986) reported a less successful study in which 12 epileptic patients were given 200-300 mg of cannabidiol per day, in addition to standard antiepileptic drugs. There seemed to be no significant improvement in seizure frequency.

Trembly et al (1990) reports an open trial with a single patient who was given 900-1200 mg of cannabidiol a day for 10 months. This trial showed seizure frequency was markedly reduced in the patient.

It is perhaps significant that some 20 years since these trials there has been no further development. This could be down to a number of factors including a general prejudice against medicines based on *cannabis*. It is also possible that the dose levels used in the trials were not optimal and the applicant has determined that cannabinoids may produce bell shaped dose response curves.

In addition to the disclosures suggesting CBD may be beneficial there is a report (Davis & Ramsey) of tetrahydrocanibinol (THC) being administered to 5 institutionalized children who were not responding to their standard treatment (phenobarbital and phenoytin). One became entirely free of seizures, one became almost completely free of seizures, and the other three did no worse than before.

However, there are more than forty recognisable types of epileptic syndrome partly due to seizure susceptibility varying from patient to patient (McCormick and Contreras, 2001, Lutz, 2004) and a challenge is finding drugs effective against these differing types.

Neuronal activity is a prerequisite for proper brain function. However, disturbing the excitatory-inhibitory equilibrium of neuronal activity may induce epileptic seizures. These epileptic seizures can be grouped into two basic categories: partial and generalised seizures. Partial seizures originate in specific brain regions and remain localised— most commonly the temporal lobes (containing the hippocampus), whereas generalised seizures appear in the entire forebrain as a secondary generalisation of a partial seizure (McCormick and Contreras, 2001, Lutz, 2004). This concept of partial and generalised seizure classification did not become common practice until the International League Against Epilepsy published a classification scheme of epileptic seizures in 1969 (Merlis, 1970, Gastaut, 1970, Dreifuss et al., 1981).

The International League Against Epilepsy further classified partial seizures, separating them into simple and complex, depending on the presence or the impairment of a consciousness state (Dreifuss et al., 1981).

The league also categorized generalised seizures into numerous clinical seizure types, some examples of which are outlined below:

Absence seizures occur frequently, having a sudden onset and interruption of ongoing activities. Additionally, speech is slowed or impeded with seizures lasting only a few seconds (Dreifuss et al., 1981).

Tonic-clonic seizures, often known as "grand mal", are the most frequently encountered of the generalised seizures (Dreifuss et al., 1981). This generalised seizure type has two stages: tonic muscle contractions which then give way to a clonic stage of convulsive movements. The patient remains unconscious throughout the seizure and for a variable period of time afterwards.

Atonic seizures, known as "drop attacks", are the result of sudden loss of muscle tone to either a specific muscle, muscle group or all muscles in the body (Dreifuss et al., 1981).

The onset of epileptic seizures can be life threatening with sufferers also experiencing long-term health implications (Lutz, 2004). These implications may take many forms:
- mental health problems (e.g. prevention of normal glutamatergic synapse development in childhood);
- cognitive deficits (e.g. diminishing ability of neuronal circuits in the hippocampus to learn and store memories);
- morphological changes (e.g. selective loss of neurons in CA1 and CA3 regions of hippocampus in patients presenting mesial temporal lobe epilepsy as a result of excitotoxicity) (Swann, 2004, Avoli et al., 2005)

It is noteworthy that epilepsy also greatly affects the lifestyle of the sufferer—potentially living in fear of consequential injury (e.g. head injury) resulting from a grand mal seizure or the inability to perform daily tasks or the inability to drive a car unless having had a lengthy seizure-free period (Fisher et al., 2000).

Three well-established and extensively used in vivo models of acute seizure, which mimic the neuronal activity and consequent physical symptoms that manifest in a seizure suffered by someone with epilepsy, are:
- pentylenetetrazole-induced model of generalised seizures (Obay et al., 2007, Rauca et al., 2004);
- pilocarpine-induced model of temporal lobe (i.e. hippocampus) seizures (Pereira et al., 2007); and
- penicillin-induced model of partial seizures (Bostanci and Bagirici, 2006).

These provide a range of seizure and epilepsy models, essential for therapeutic research in humans.

It is an object of the present invention to identify phyto-cannabinoids or combinations of phyto-cannabinoids which have use in treating specific forms of seizure associated with epilepsy.

It is another object of the present invention to determine dose ranges which are likely to prove effective and identify combinations of cannabinoids (as might be present in different *cannabis* chemotypes or varieties) which are likely to prove more beneficial due to likely differences in their mechanisms of action.

BRIEF SUMMARY OF THE DISCLOSURE

In accordance with a first aspect of the present invention there is provided one or a plurality of phytocannabinoids selected from the group consisting of tetrahydrocannabivarin (THCV) and cannabidiol (CBD) for use in the treatment of generalised seizures and/or partial seizure.

Preferably the medicament is to treat clonic and/or tonic seizures.

The preferred daily dose of THCV is at least 1.5 mg, more preferably at least 5 mg through 10 mg to 15 mg or more.

Preferably the THCV is used in combination with at least a second, therapeutically effective cannabinoid, preferably CBD.

The CBD is preferably present in an amount which will provide a daily dose of at least 400 mg, more preferably at least 600 mg and as much as 800 mg or more, but preferably less than 1200 mg.

The cannabinoids may be present as pure or isolated cannabinoids or in the form of plant extracts. Where a plant extract is used it is preferable that the THC content is less than 5% by weight of the total cannabinoids, more preferably less than 4% through 3%, 2% and 1%. THC can be selectively removed from extracts using techniques such as chromatography.

The invention also extends to using a phyto-cannabinoid in the manufacture of a medicament to treat a specific form of epilepsy.

In accordance with a second aspect of the present invention there is provided a composition for use in treating generalised seizures and/or partial seizure comprising THCV and or CBD The composition preferably takes the form of a plant extract containing one or more phytocannabinoids and one or more excipients.

In accordance with a third aspect of the present invention there is provided THCV and/or CBD for use in the manufacture of a medicament for use in the treatment of generalised seizures and/or partial seizure.

In accordance with a forth aspect of the present invention there is provided a method of treating generalised seizures and/or partial seizure comprising administering to a patient a medicament comprising an effective amount of THCV and/or CBD.

The combined use is predicated on apparent different mechanisms of action given the different results observed in different animal models and at different doses.

BRIEF DESCRIPTION OF THE DRAWINGS

Embodiments of the invention are further described hereinafter with reference to the accompanying drawings, in which

FIG. 16 A-D describes the percentage of animals in each group that reached specified seizure states. Significant differences vs control were assessed using a binomial test. P≤0.05 (*); P≤0.001 (***);

FIG. 19 A-B describes the effects of CBD upon tonic-clonic seizures without postural control. A: % of animals that experienced tonic-clonic seizures without postural control. B: frequency with which animals displayed tonic-clonic seizures without postural control in the two hour recording period (or until death). A: binomial statistical test; B: one-way ANOVA followed by Tukey test. , * and # indicate p≤0.01, 0.001 and 0.1 respectively; and FIG. 20 A-C describes the effect of CBD on penicillin-induced seizure severity and mortality. A: Median severity of seizures (grey line), also shown is the 25th and 75th percentiles (black horizontal lines) and the maximum and minimum values (upward and downward error bars respectively). B: Percentage of animals that remained seizure free throughout. C: Percentage mortality. A: one-way ANOVA followed by Tukey test. B&C: binomial statistical test; *, *** and # indicate p≤0.05, 0.001 and 0.1.

DETAILED DESCRIPTION

PTZ Model—Examples 1-3

General Methodology for PTZ Model

Animals

Figure 1:
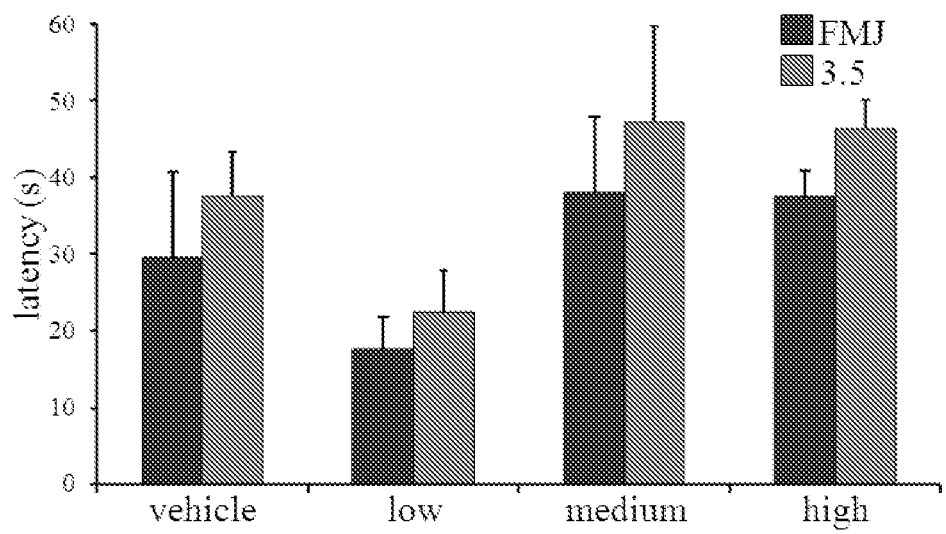
FIG. 1 shows latencies to initial and later seizure severities. The mean latencies to first myoclonic jerk (FMJ) and scores of 3.5 are shown ±S.E.M. for vehicle or for low, medium or high doses of THCV BDS and 70 mg/kg PTZ. n=8-10.

Male Wistar rats (P24-29; 75-110 g) were used to assess the effects of the cannabinoids: THCV (BDS and pure) and CBD on the PTZ model of generalised seizures. Animals were habituated to the test environment, cages, injection protocol and handling prior to experimentation. Animals were housed in a room at 21° C. on a 12 hour light: dark cycle (lights on 0900) in 50% humidity, with free access to food and water.

Experimental Setup

Five 6 L Perspex tanks with lids were placed on a single bench with dividers between them. Closed-circuit television (CCTV) cameras were mounted onto the dividers to observe rat behaviour. Sony Topica CCD cameras (Bluecherry, USA) were linked via BNC cables to a low-noise PC via Brooktree digital capture cards (Bluecherry, USA). Zoneminder (http://www.zoneminder.com) software was used to monitor rats, start and end recordings and manage video files. In-house Linux scripts were used to encode video files into a suitable format for further offline analysis using The Observer (Noldus Technologies).

Dose

A range of doses of PTZ (50-100 mg/kg body weight) were used to determine the best dose for induction of seizures (see below). As a result, doses of 70 and 80 mg/kg injected intra-peritoneally (IP; stock solution 50 mg/ml in 0.9% saline) were used to screen the cannabinoids.

Experimental Protocols

On the day of testing, animals received an IP injection with either the cannabinoids (low, medium or high dose) or a matched volume of the cannabinoids vehicle (1:1:18 ethanol:Cremophor: 0.9% w/v NaCl solution), which served as the negative control group. Animals were then observed for 30 mins, after which time they received an IP injection of 70 or 80 mg/kg PTZ. Negative vehicle controls were performed in parallel with cannabinoid-dosed subjects. After receiving a dose of PTZ, animals were observed and videoed to determine the severity of seizure and latency to several seizure behaviour types (see in vivo analysis, below). Animals were filmed for half an hour after last sign of seizure, and then returned to their cage.

In Vivo Analysis

Animals were observed during experimental procedures, but all analysis was performed offline on recorded video files using The Observer behavioural analysis software (Noldus, Netherlands). A seizure severity scoring system was used to determine the levels of seizure experienced by subjects (Pohl & Mares, 1987). All signs of seizure were detailed for all animals.

TABLE 1

Seizure severity scoring scale, adapted from Pohl & Mares, 1987.

| Seizure score | Behavioural expression | Righting reflex |
|---|---|---|
| 0 | No changes to behaviour | Preserved |
| 0.5 | Abnormal behaviour (sniffing, excessive washing, orientation) | Preserved |
| 1 | Isolated myoclonic jerks | Preserved |
| 2 | Atypical clonic seizure | Preserved |
| 3 | Fully developed bilateral forelimb clonus | Preserved |
| 3.5 | Forelimb clonus with tonic component and body twist | Preserved |
| 4 | Tonic-clonic seizure with suppressed tonic phase | Lost |
| 5 | Fully developed tonic-clonic seizure | Lost |
| 6 | Death | |

Latency from Injection of PTZ to Specific Indicators of Seizure Development:

The latency (in s) from injection of PTZ to first myoclonic jerk (FMJ; score of 1), and to the animal attaining "forelimb clonus with tonic component and body twist" (score of 3.5) were recorded. FMJ is an indicator of the onset of seizure activity, whilst >90% of animals developed scores of 3.5, and so is a good marker of the development of more severe seizures. Data are presented as the mean±S.E.M. within an experimental group.

Maximum Seizure Severity:

This is given as the median value for each experimental group based on the scoring scale below.

% Mortality:

The percentage of animals within an experimental group that died as a result of PTZ-induced seizures. Note that the majority of animals that developed tonic-clonic seizures (scores of 4 and 5) in the THCV (BDS) study died as a result, and that a score of 6 (death) automatically denotes that the animal also experienced tonic-clonic seizures.

Seizure Duration:

The time (in seconds) from the first sign of seizure (typically FMJ) to either the last sign of seizure or, in the case of subjects that died, the time of death—separated into animals that survived and those that did not. This is given as the mean±S.E.M. for each experimental group.

Statistics:

Differences in latencies and durations were assessed by one-way analysis of variance (ANOVA) with post-hoc Tukey's test. $P \leq 0.05$ was considered significant.

Example 1

THCV (BDS)

The THCV BDS comprised a whole extract of a chemovar in which THCV was the predominant cannabinoid. (i.e. it was the major cannabinoid present in the extract, 80% by weight of the total cannabinoid content). THC was the second most prevalent cannabinoid, and was present in significant amounts. (i.e. it comprised greater than 10% by weight of the total cannabinoid content, being present at about 16%), and there were a number of minor cannabinoids identified, each comprising less than 2% by weight of the total cannabinoid content as measured by HPLC analysis. The ratio of THCV to THC in this extract is about 5:1.

In fact the THCV content was 67.5% by weight of the extract and the THC content was 13.6% by weight of the extract, with the other identified cannabinoids in total comprising about 3% by weight of the extract, the remaining 16% comprising non-cannabinoids.

PTZ Pilot Study

Seizures induced by a range of PTZ concentrations (50-100 mg/kg; the range present in the literature) in rats were investigated to determine an optimal dose prior to the investigation of the cannabinoid effect. PTZ doses of:

50 mg/kg and 60 mg/kg induced very little seizure-like activity (n=4);

70 mg/kg typically induced clonic seizures (score of 3.5; 8 of 13 subjects);

80 mg/kg regularly induced tonic-clonic seizures (scores of 4 and 5; 6 of 10 subjects).

Additionally, it was found that repeated dosing with PTZ resulted in increased sensitivity over time; therefore no experiments were performed on animals that had already received a dose of PTZ.

The effect of THCV BDS on PTZ-induced seizures was first assessed against a PTZ dose of 70 mg/kg. As described below, this yielded a vehicle control group that did not typically experience severe seizure scores. Therefore THCV BDS was also screened against an 80 mg/kg dose of PTZ. It was felt that the increased seizure severity experienced by vehicle control animals exposed to 80 mg/kg PTZ was a more appropriate test of potential anti-convulsant activity.

Effect of THCV BDS on Moderately Severe (70 mg/kg) PTZ-Induced Seizures

Three doses of THCV BDS were assessed against a concentration of PTZ known to induce moderate seizures in rats (70 mg/kg; see pilot, above). The low, medium and high doses of THCV BDS used were 0.37, 3.70 and 37.04 mg/kg, and yielded actual THCV doses of 0.25, 2.5 and 25 mg/kg respectively. These doses were matched by THCV content to those being used for screening pure THCV against PTZ-induced seizures.

Figure 2:
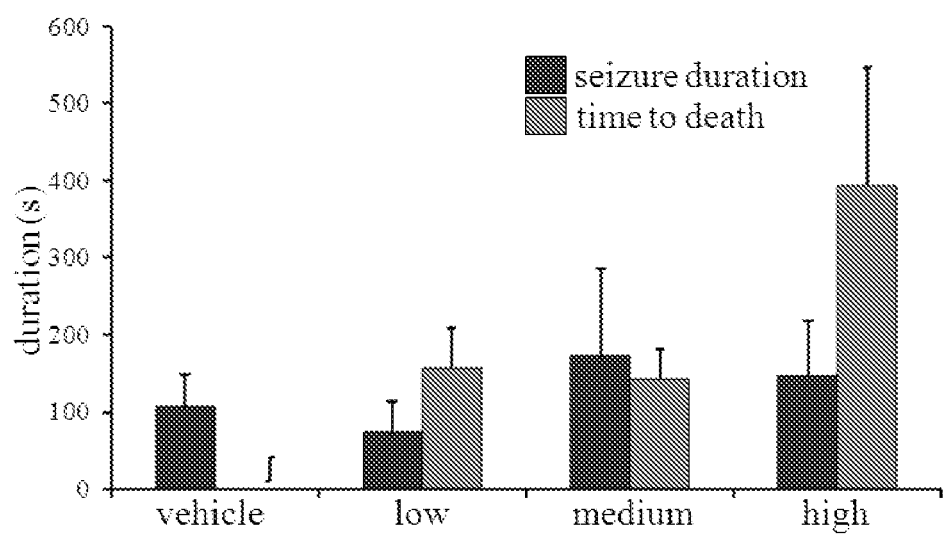
FIG. 2 shows seizure duration and time to death. The mean durations of seizures in animals that survived, and the time from first seizure sign to death in those that died, are shown ±S.E.M. for vehicle or for low, medium or high doses of THCV BDS and 70 mg/kg PTZ. n=3-10 dependent on proportions of animals that died within experimental groups. ƒ=vehicle group had no deaths and so no value is shown here.

THCV BDS did not have any significant effects on latency to first myoclonic jerk or on latency to attaining a severity score of 3.5 on the seizure severity scale (FIG. 1). It should be noted that although values for both these variables were higher for animals treated with medium and high dose THCV BDS compared to control, this failed to reach significance (P>0.05). Similarly, no significant impact on duration of seizure was seen (FIG. 2).

The effects of THCV BDS on seizure severity (FIG. 3) and mortality (FIG. 4) in animals that received doses of 70 mg/kg PTZ did not conform to a simple pattern. No animal injected with vehicle-alone exceeded the median severity score of 3.5 for that group, and no animals died (n=10).

Figure 3:
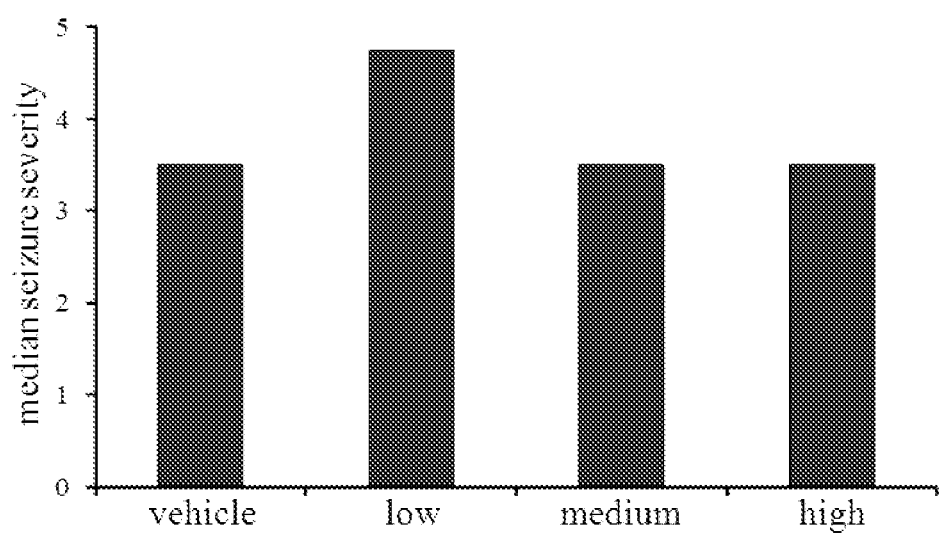
FIG. 3 shows median severity scores. Median severity scores for groups of animals treated with vehicle or with low, medium or high doses of THCV BDS prior to 70 mg/kg PTZ. n=10 for all groups.
Figure 4:
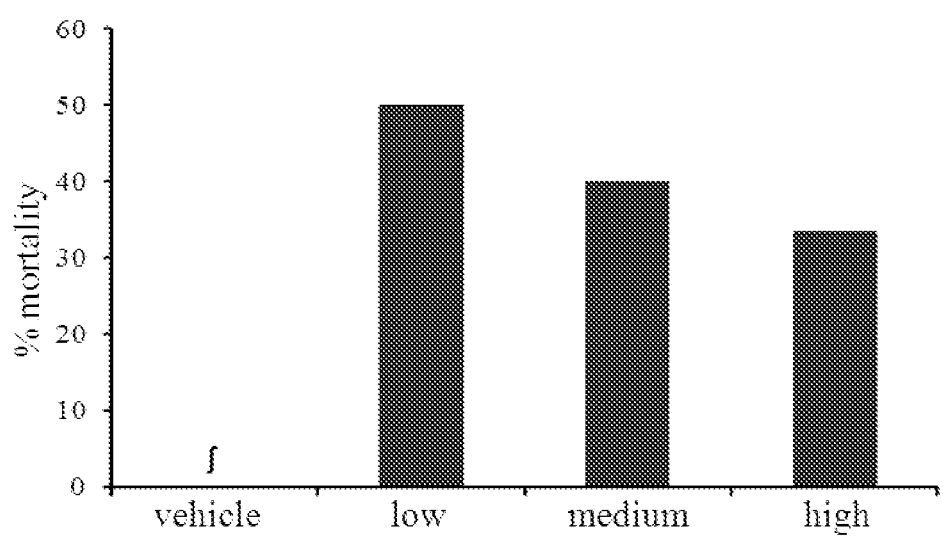
FIG. 4 shows mortality rates. Mortality rates expressed as percentages for animals treated with vehicle or with low, medium or high doses of THCV BDS and 70 mg/kg PTZ. n=10 for all groups. ƒ=vehicle group had no deaths, therefore no value is shown.

In contrast, 70 mg/kg PTZ induced severe tonic-clonic seizures and death in 50% of animals injected with a low dose of THCV BDS, demonstrating a median severity score of 4.75. This increase in severity was not significant. However, animals injected with medium and high doses of THCV BDS exhibited a lower median severity score and lower mortality rates than those exposed to low doses (FIGS. 3 & 4). Medium and high dose mortality rates were higher than that of the vehicle group, but not significantly so (P>0.05; FIG. 4). However, median severity scores were the same between medium & high doses (FIG. 3). This pattern of results suggested that a further set of experiments, in which THCV BDS was screened against a dose of PTZ which would induce severe seizures in control (vehicle-treated) animals, was required.

Effect of THCV BDS on Severe (80 mg/kg) PTZ-Induced Seizures

Figure 5:
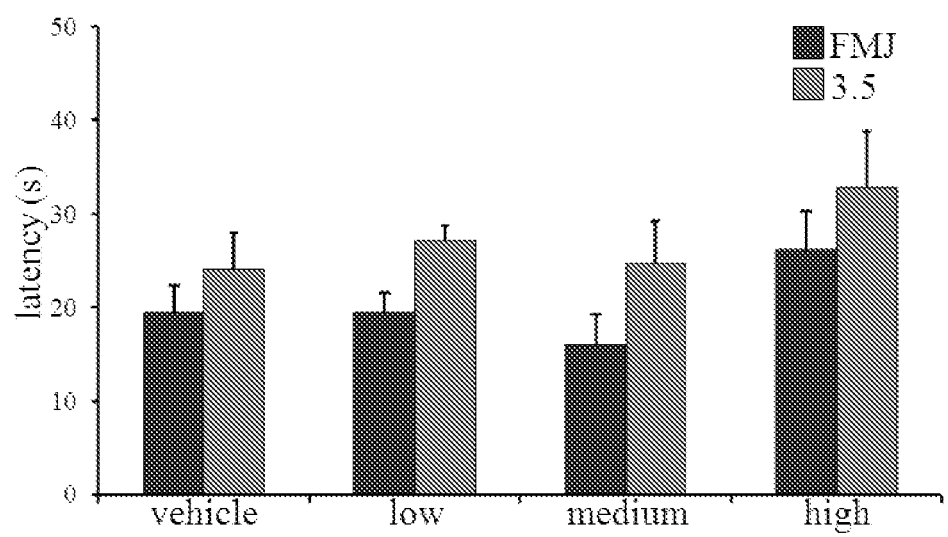
FIG. 5 shows latencies to initial and later seizure severities. The mean latencies to first myoclonic jerk (FMJ) and scores of 3.5 are shown ±S.E.M. for vehicle or for low, medium or high doses of THCV BDS and 80 mg/kg PTZ. n=7-10.
Figure 6:
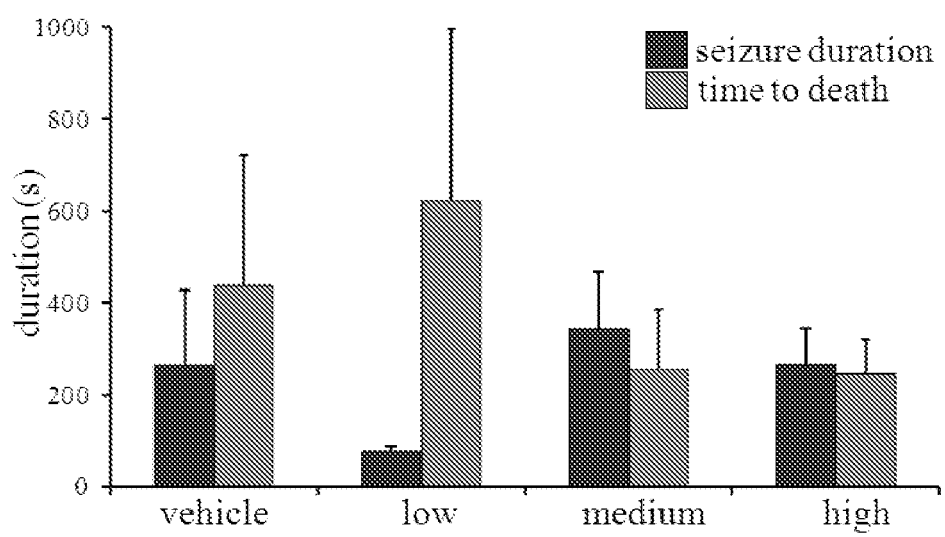
FIG. 6 shows seizure duration and time to death. The mean durations of seizures in animals that survived, and the time from first seizure sign to death in those that died, are shown ±S.E.M. for vehicle or for low, medium or high doses of THCV BDS and 80 mg/kg PTZ. n=3-7 dependent on proportions of animals that died within experimental groups.

The effects of the same three doses of THCV BDS on seizures induced by 80 mg/kg PTZ were assessed. It is worth noting that 80 mg/kg induced significantly more severe seizures than 70 mg/kg in vehicle control groups (P=0.009), with median seizure severity scores of 6 and 3.5 respectively. THCV BDS did not have a significant effect on latencies to FMJ or a severity score of 3.5 (FIG. 5). Similarly, no effect was observed on seizure durations (FIG. 6).

Figure 7:
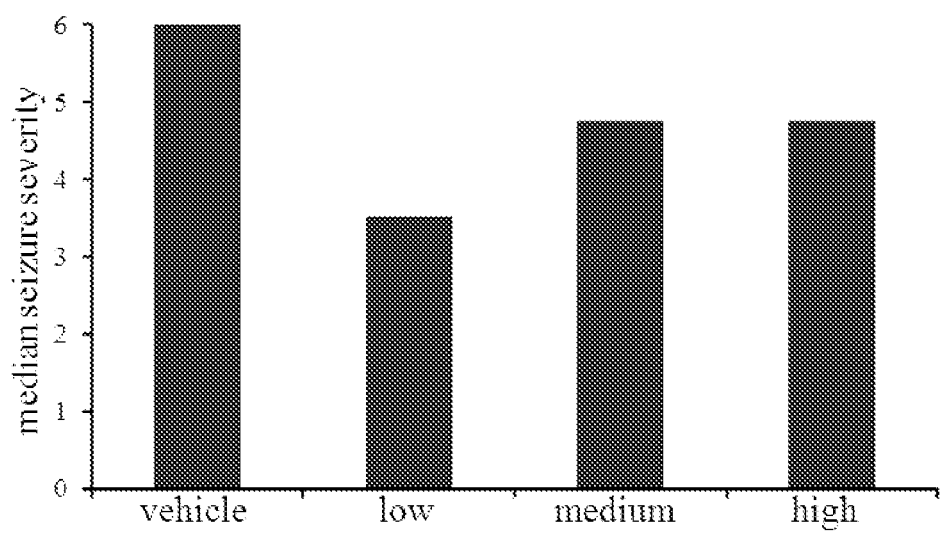
FIG. 7 shows median severity scores. Median severity scores for groups of animals treated with vehicle or with low, medium or high doses of THCV BDS prior to 80 mg/kg PTZ. n=10 for all groups.
Figure 8:
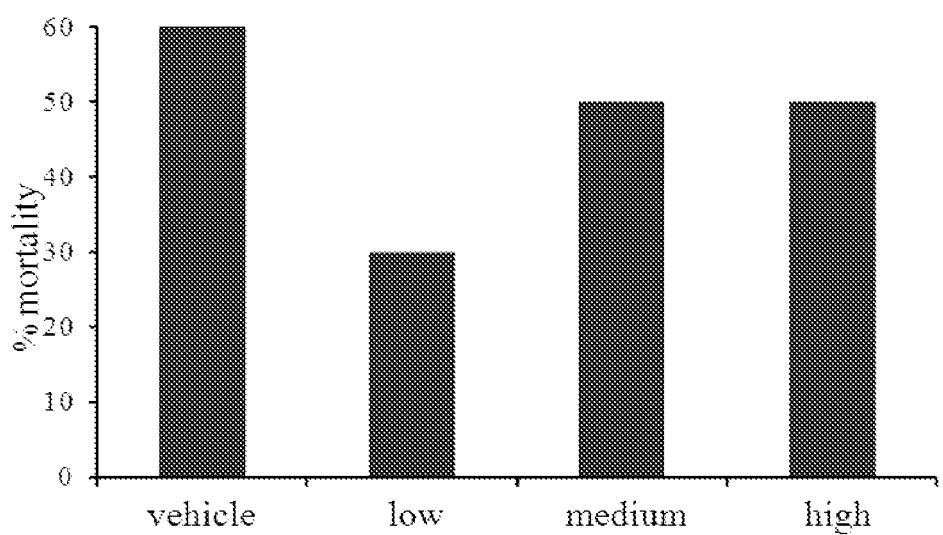
FIG. 8 shows mortality rates. Mortality rates expressed as percentages for animals treated with vehicle or with low, medium or high doses of THCV BDS and 80 mg/kg PTZ. n=10 for all groups.

Low dose THCV BDS decreased both seizure severity (FIG. 7) and mortality (FIG. 8) in animals that received doses of 80 mg/kg PTZ. Animals that received low THCV BDS had a lower median severity score (3.5 compared to 6) than vehicle controls. However, this difference was not significant (P>0.5). The low THCV BDS dose group also had a mortality rate half that of the vehicle control group (30% vs 60%).

Groups treated with medium and high doses of THCV BDS had a lower seizure severity score of 4.75 (P>0.5 vs control), and a lower mortality rate of 50%, compared to 6 and 60% respectively.

In Vivo Summary and Conclusion

Screening of THCV BDS in the PTZ model did not appear to have any significant anti- or pro-convulsant effects on either moderate or severe PTZ-induced seizures. However, a trend towards lower severity and mortality was seen in animals that received a low dose of THCV BDS prior to induction of severe (80 mg/kg PTZ) seizures, compared to vehicle controls.

It is possible that this effect is masked at higher doses of THCV BDS by higher levels of other cannabinoid constituents (such as THC) present in the non-THCV content of the THCV BDS. Higher doses of THCV BDS will contain increasing doses of non-THCV content, such as THC, which may oppose any potential positive effects of THCV.

Example 2

THCV (Pure)

Effect of Pure THCV Against PTZ-Induced Seizures

Low (0.025 mg/kg), medium (0.25 mg/kg) and high (2.5 mg/kg) doses of pure THCV were assessed for their effects on PTZ-induced seizures. It is worth noting at this point, for comparisons to Example 1 (THCV BDS), that differing doses of pure THCV were used compared to THCV BDS. See Table 2 below.

TABLE 2

| Comparison of THCV BDS and pure THCV doses used in PTZ model | | | |
|---|---|---|---|
| Test CB | "low" dose (mg/kg) | "medium" dose (mg/kg) | "high" dose (mg/kg) |
| THCV BDS | 0.25 | 2.5 | 25 |
| Pure THCV | 0.025 | 0.25 | 2.5 |

Values given are for effective THCV content of doses (therefore actual doses of THCV BDS are approx 1.5 times larger).

80 mg/kg PTZ successfully induced seizures of varying severities in animals from all 4 experimental groups (n=16 per group). PTZ-induced seizures led to the death of 44% of animals that received vehicle alone. Groups that received low, medium and high THCV all exhibited lower mortality rates of 41%, 33% and 38% respectively; however these values were not significantly different from that of the vehicle group (p>0.05, binomial test).

The mean values for latency to first seizure sign, and to scores of [3] and [5] on the seizure scoring scale used, as well as the duration of seizure for surviving animals, are described in FIGS. 9A-D.

It can be seen that seizures started later, as shown by increased latency to first manifestation of seizure-like behaviour (FIG. 9A) in animals that received THCV compared to vehicle controls.

The delay of onset was significant at the highest dose of THCV (p=0.02). A similar pattern was seen for latencies to scores of [3] and [5](FIGS. 9B and 9C) with all THCV doses exhibiting increased latencies, reaching a significant level at the highest dose of THCV (p=0.017 and 0.013 for [3] and [5] respectively).

Figure 9:
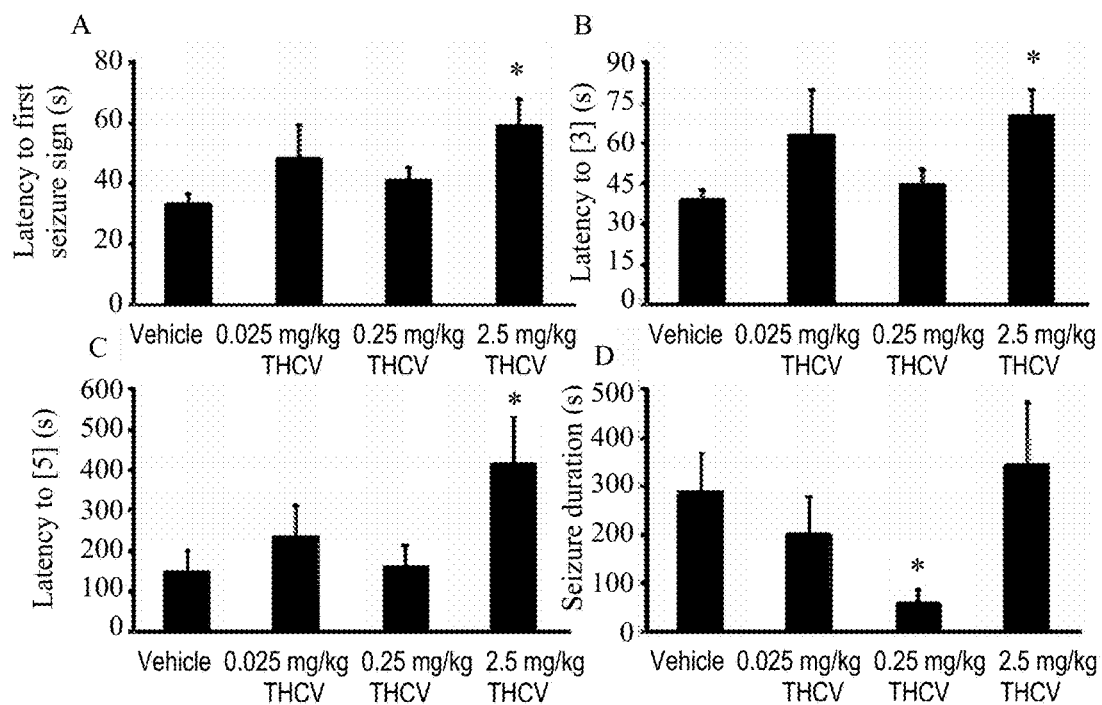
FIG. 9 A-D show PTZ-induced seizure development and duration with pure THCV. A, B and C show the mean latency (s) from injection of 80 mg/kg PTZ to: first sign of seizure (A); development of myoclonic seizures (B) and full tonic-clonic seizures (C) for vehicle and THCV-dosed groups. n=5-16 depending on incidence of each marker within a specific group). (D) shows the mean duration of seizures (s) in animals that survived post-seizure. All values ±S.E.M., * indicates significant difference from vehicle group (P<0.05; Mann-Whitney U test)

It was also observed that duration of PTZ-induced seizures in animals that survived the experimental period were significantly shorter after administration of the medium dose of THCV compared to vehicle controls (FIG. 9D; p=0.03).

Table 3 below displays the values for median seizure severity in each experimental group.

TABLE 3

| Seizure severity and incidence | | | | |
|---|---|---|---|---|
| | Vehicle | 0.025 mg/kg THCV | 0.25 mg/kg THCV | 2.5 mg/kg THCV |
| Median severity | 4.25 | 3.5 | 3.5 | 3.5 |
| % no seizure | 12.5 | 5.9 | 33.3* | 18.8 |

The median maximum severities and % of animals that did not experience any signs of seizure for each experimental group are given (n=16 for each value). * indicates significant difference from vehicle group (binomial significance test, P<0.05).

Vehicle control animals exhibited a median seizure severity of 4.25, whereas all groups which received THCV had a median severity score of 3.5. This decrease was not significantly different.

12.5% vehicle control animals displayed no indicators of seizure, suggesting these animals did not develop seizures after PTZ administration. A significantly higher number of animals (33.3%) displayed no signs of seizure in the group that received 0.25 mg/kg (Table 3; p=0.031). This data suggests that the medium dose of 0.25 mg/kg THCV protected against the development of seizures.

In Vivo Summary and Conclusion

The effects of the high dose of THCV on latency values suggest that THCV can delay both onset and seizure development, whilst the significant effects of the medium dose on the incidence of seizure at medium (0.25 mg/kg) THCV doses suggest a significant anticonvulsive action on PTZ-induced seizures.

Example 3

CBD (Pure)

In addition to THCV, CBD was also screened in the PTZ model. The results strongly indicate that CBD (at levels of 100 mg/kg) in this model is anti-convulsant as it significantly decreased the mortality rate and incidence of the most severe seizures compared to vehicle control animals.

Effect of Pure CBD Against PTZ-Induced Seizures

Pure CBD was injected intra-peritoneally (IP) in the standard vehicle (1:1:18 ethanol:Cremophor:0.9% w/v NaCl) at doses of 1, 10 and 100 mg/kg alongside animals that received vehicle alone at a matched volume (n=15 for each group). 60 minutes later PTZ (80 mg/kg, IP) was administered.

Figure 10:
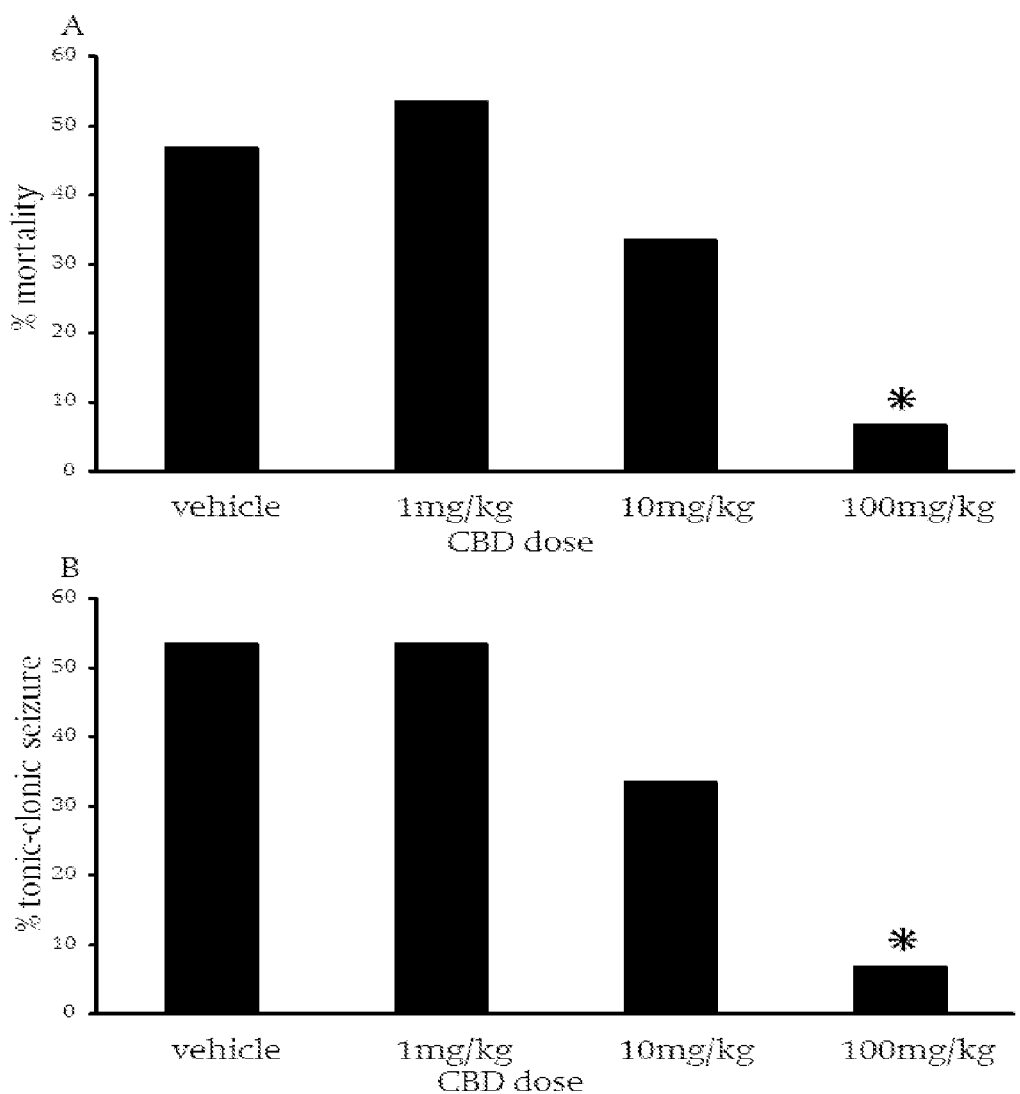
FIG. 10 A-B show the effect of CBD on PTZ-induced seizures A: % mortality experienced as a result of IP injection of 80 mg/kg PTZ in vehicle and CBD-dosed (1, 10,100 mg/kg CBD) animals (n=15 for all groups). B: % of vehicle- and CBD-dosed (1, 10,100 mg/kg CBD) animals that experienced tonic-clonic seizures as a result of IP injection of 80 mg/kg PTZ. * indicates significant result (p<0.01)

46.7% of control animals that received vehicle alone died within 30 minutes of PTZ administration (FIG. 10). In contrast only 6.7% (only 1 of 15) of animals that received 100 mg/kg CBD died, a marked reduction that proved to be significant ($p<0.001$).

Additionally only 6.7% of animals that received 100 mg/kg CBD experienced the most severe seizures (score of 5) in comparison to 53.3% of vehicle control animals, a decrease that was also significant ($p<0.001$; FIG. 10 in vivo).

In contrast to pure THCV, no significant increases in latency of seizure development were observed. However, the marked and significant reductions indicate a striking anti-convulsant effect on PTZ-induced seizures.

Screening and analysis of pure CBD in the PTZ model at high dose (100 mg/kg) of CBD on mortality levels and incidence of the most severe seizures suggests that CBD can attenuate the severity of PTZ-induced seizures Pilocarpine Model—Examples 4 and 5

Example 4

Pure THCV

Effect of Pure THCV Against Pilocarpine-Induced Seizures

Figure 11:
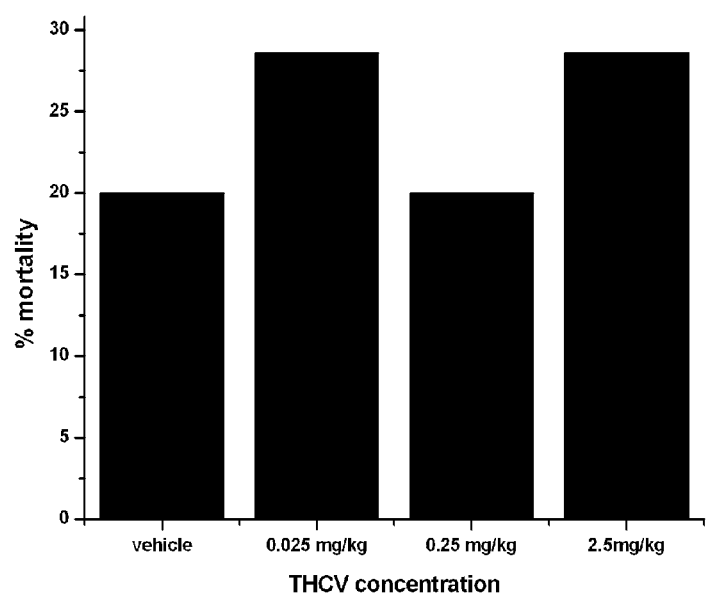
FIG. 11 shows the lack of effect of THCV on the percentage mortality. Significance assessed using a binomial test by comparison with control and significance accepted at P<0.05. No significant difference vs control was found at any dose.

Pure THCV was injected intra-peritoneally (IP) in the standard vehicle (1:1:18 ethanol:Cremophor:0.9% w/v NaCl) at doses of 0.025, 0.25 and 2.5 mg/kg alongside animals that received vehicle alone at a matched volume (n≥14 for each group). 15 minutes later methylscopolamine (1 mg/kg; to reduce peripheral muscarinic effects of pilocarpine) was administered followed, 45 minutes later by pilocarpine (380 mg/kg, IP) administration.
Results No significant effect of THCV at any dose was observed upon latency to the onset of seizure ($P>0.5$ for all doses vs control; 1-way ANOVA with Tukey's post-hoc test). No significant change in percentage mortality vs control was seen for any THCV dose (FIG. 11).

Figure 12:
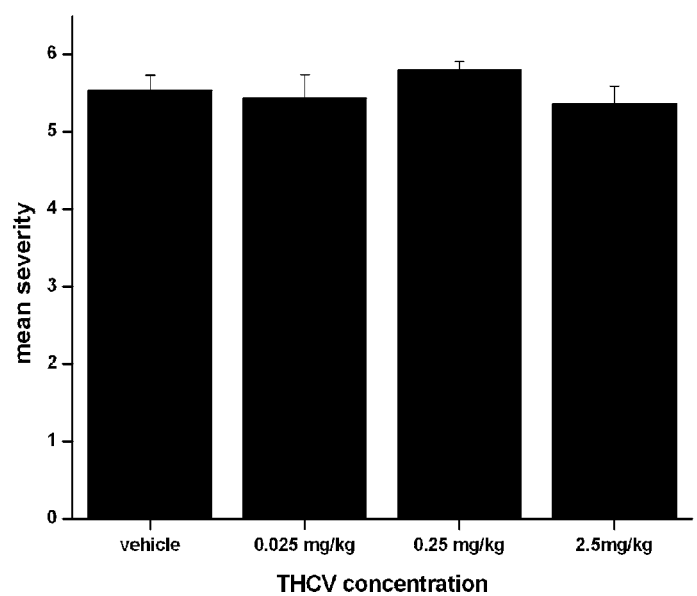
FIG. 12 shows the lack of effect of THCV on the mean maximum seizure severity. Significance was assessed by 1-way ANOVA with Tukey's post-hoc test; P>0.5 for all comparisons vs control.
Figure 13:
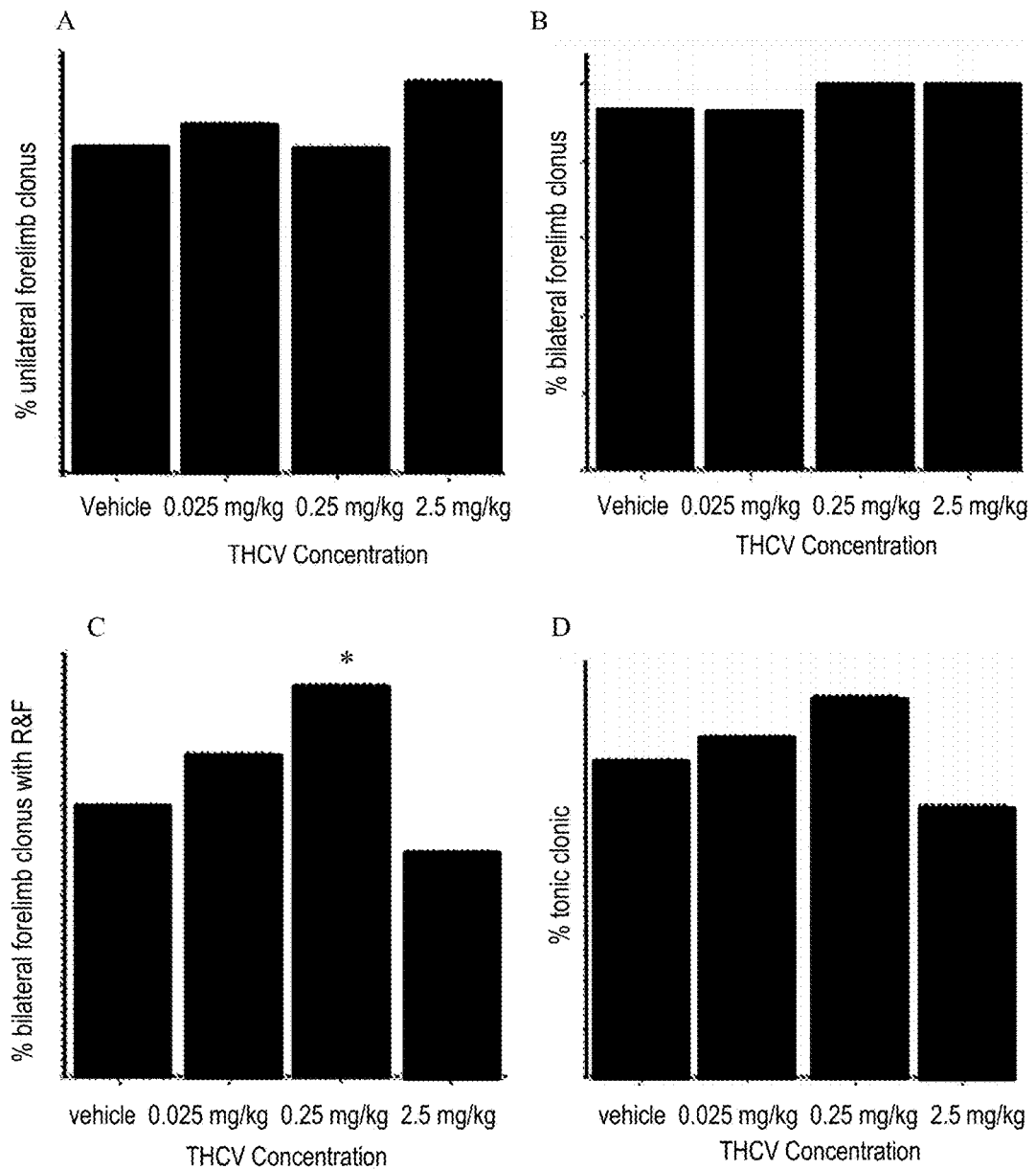
FIG. 13 A-D shows the percentage of animals in each group that reached specified seizure states when treated with THCV. Significant differences vs control were assessed using a binomial test. P≤0.05.

In addition THCV had no effect upon the mean maximum severity of seizure reached per animal group (FIG. 12).

The percentage of animals in each group that reach a particular seizure state (unilateral forelimb clonus, bilateral forelimb clonus, bilateral forelimb clonus with rearing and falling and tonic-clonic) was also assessed (FIG. 13A-D).

THCV caused no significant changes in the percentage of animals showing unilateral forelimb clonus, bilateral forelimb clonus or tonic-clonic seizures at any dose. Interestingly, 0.25 mg/kg THCV caused a significant increase in the percentage of animals showing bilateral forelimb clonus with rearing and falling although this effect was not seen at any other dose.

Example 5

Pure CBD

Effect of Pure CBD Against Pilocarpine-Induced Seizures

Figure 14:
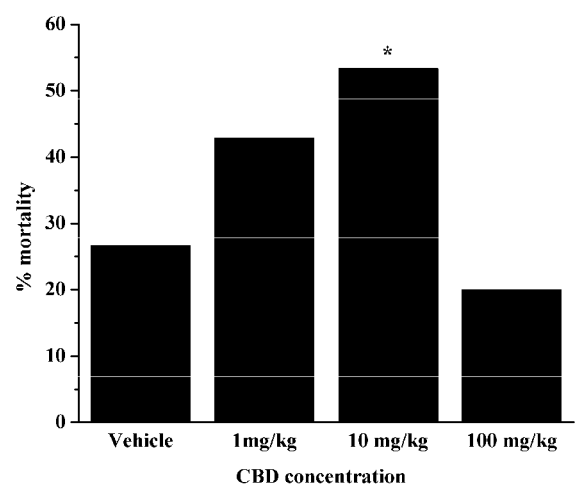
FIG. 14 shows the effect of CBD on the percentage mortality. Significance assessed by binomial test; * shows a significant increase in mortality (P<0.05). Note that this effect only appeared at 10 mg/kg and was lost at 100 mg/kg, suggestive of a biphasic effect.

Pure CBD was injected intra-peritoneally (IP) in the standard vehicle (1:1:18 ethanol:Cremophor:0.9% w/v NaCl) at doses of 1, 10 and 100 mg/kg alongside animals that received vehicle alone at a matched volume (n≥14 for each group). 15 minutes later methylscopolamine (1 mg/kg; to reduce peripheral muscarinic effects of pilocarpine) was administered followed, 45 minutes later by pilocarpine (380 mg/kg, IP) administration.
Results No significant effect of CBD at any dose was observed upon latency to the onset of seizure ($P>0.5$ for all doses vs control; 1-way ANOVA with Tukey's post-hoc test). A significant increase in percentage mortality vs control was seen for the 10 mg/kg CBD dose as shown in FIG. 14.

Figure 15:
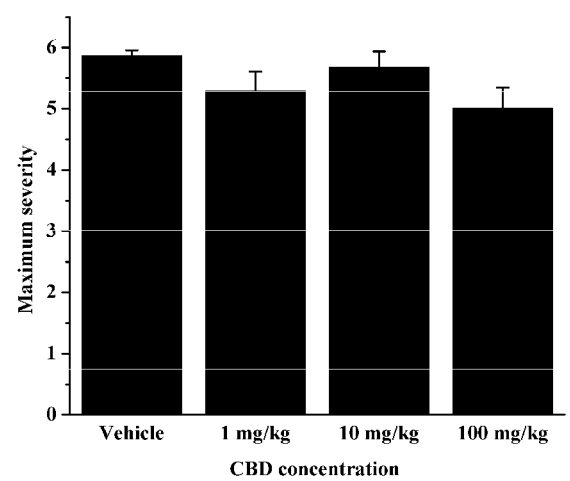
FIG. 15 shows the mean maximum seizure severity. Significance was assessed by 1-way ANOVA with Tukey's post-hoc test; P>0.5 for all comparisons vs control.

FIG. 15 details that CBD had no effect upon the mean maximum severity of seizure reached per animal group.

FIGS. 16 A-D detail the percentage of animals in each group that reached particular seizure states (unilateral forelimb clonus, bilateral forelimb clonus, bilateral forelimb clonus with rearing and falling and tonic-clonic).

CBD caused significant decreases in the percentage of animals showing unilateral forelimb clonus at CBD doses >1 mg/kg, Interestingly, although no significant differences in the percentage of animals exhibiting bilateral forelimb clonus were found, the percentage of animals manifesting with bilateral forelimb clonus with rearing and falling were significantly reduces at all CBD doses >1 mg/kg. The percentage of animals exhibiting tonic-clonic seizures was significantly reduced at CBD doses of 1 mg/kg and 100 mg/kg but not 10 mg/kg (c.f. FIG. 14).

Figure 17:
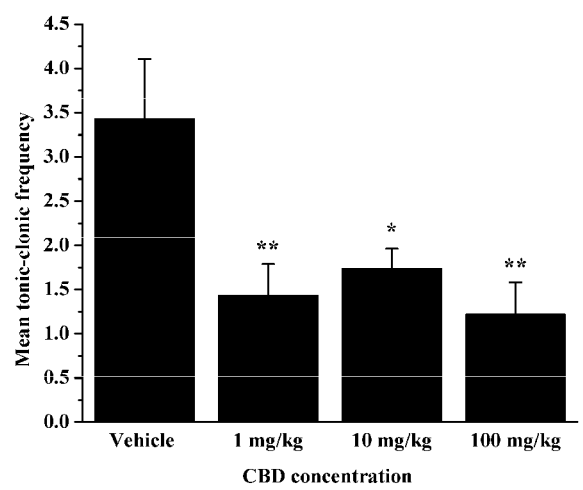
FIG. 17 shows the effects of CBD upon mean tonic-clonic frequency. Significance was assessed using a one way ANOVA with Tukey's post-hoc test. P≤0.05 (*); P≤0.01 (**)

The effects of CBD upon tonic-clonic seizure events by examining the mean frequency of tonic-clonic events as is shown in FIG. 17. CBD caused a significant reduction in mean tonic-clonic frequency at all doses tested. CBD effects upon the mean frequency of all other seizure scores were also assessed in the same way but no significant differences vs control were found ($P>0.5$ for all).

Figure 18:
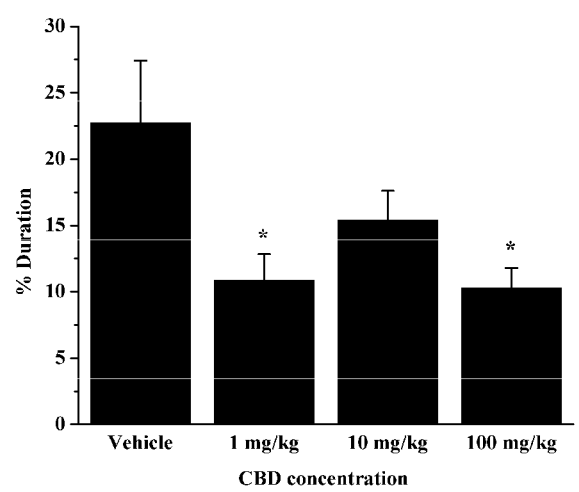
FIG. 18 describes the percentage duration of time spent in a tonic-clonic state compared to the total duration of the seizure period. Significance was assessed using a one way ANOVA with Tukey's post-hoc test. P≤0.05 (*)

The percentage duration of time spent in a tonic-clonic state compared to the total duration of the seizure period was examined (FIG. 18). CBD significantly reduced the percentage duration at doses of 1 mg/kg and 100 mg/kg but not 10 mg/kg.

Example 6

Penicillin Model—Example 6 (Only)

Example 6

Pure CBD

Effects of Pure CBD on Penicillin-Induced Seizures

CBD (1, 10 and 100 mg/kg) or CBD vehicle (1:1:18 ethanol:Cremophor: 0.9% w/v NaCl) was administered i.p. to adult male Wistar rats (>250 g). One week prior to this, animals had been surgically implanted with a cannula into the right lateral ventricle under anaesthesia. One hour after CBD administration, 150 IU penicillin was infused into the right lateral ventricle in 1.5 µl saline solution over one minute and seizure behaviour video recorded for two hours.

Following detailed examination of animal responses to penicillin alone (using data obtained from vehicle control groups, a finalised seizure scoring scale for penicillin-induced partial seizures has been derived. The following scoring system which was derived from several existing and published scoring systems for this model, will therefore be used for analysis of drug effects upon such seizures.

Seizure Scoring Scale for Penicillin-Induced Partial Seizures.

| | |
|---|---|
| 0 | Latent period |
| 1 | Wild running/leaping |
| 2 | Myoclonic phase |
| 3 | Unilateral forelimb clonus |
| 4 | Bilateral forelimb clonus |
| 5 | Tonic-clonic seizure with postural control retained |
| 6 | Tonic-clonic seizure without postural control |

Seven of the twelve vehicle-treated animals developed the most severe seizures (tonic-clonic seizures without postural control; FIG. 19 A), whereas, administration of 100 mg/kg CBD completely prevented development of these seizures in a significant manner (p=0.001). Near-significant decreases in development of these seizures were observed in animals treated with 1 and 10 mg/kg CBD (FIG. 16A, p=0.076 for both). The frequency with which animals experienced the most severe seizures was also significantly affected (ANOVA, p=0.009; FIG. 19 B), with a significant decrease compared to the vehicle group at 100 mg/kg CBD (p=0.006) and a near-significant effect at 10 mg/kg (p=0.071).

The effect of CBD treatment on seizure severity and animal mortality is described in FIG. 20 A-C. A dose of 100 mg/kg CBD significantly reduced the median severity of penicillin-induced seizures compared to vehicle-treated animals (ANOVA p=0.024; difference between vehicle and 100 mg/kg CBD p=0.012; FIG. 20 A). Interestingly, all doses of CBD (1, 10 and 100 mg/kg) significantly increased the proportion of animals that remained seizure-free (p<0.001 for all doses; FIG. 20 B). Finally, 100 mg/kg had a near-significant effect on mortality compared to vehicle (p=0.057).

OVERALL CONCLUSION

From these studies it would appear that both THCV (pure) and CBD (pure) show promise as an anti-epileptic for generalized seizure, particularly clonic/tonic seizure. The data generated for a THCV rich extract, containing other cannabinoids including significant amounts of THC, suggest that the THC may be countering the effect of the THCV and that a cannabinoid extract which contains THCV as a major or predominant cannabinoid, but which also contains minimal, or substantially no, THC would be desirable for treating epilepsy.

Furthermore the results with pure CBD suggest that an extract containing significant amounts of both THCV and CBD, but again, minimal or substantially no THC may provide an optimum combination. Accordingly it may prove desirable to prepare a THCV predominant extract in which THC is selectively, and substantially, removed (to levels of less than a few percent). This could be mixed with a CBD rich extract (which contains much lower levels of THC) in which CBD is the major and predominant cannabinoid (also with low levels of THC) to produce an extract with clearly defined, and significant levels of both THCV and CBD, but with insignificant levels of THC. Such an extract may contain other cannabinoids and the non-cannabinoid components which result from extraction, by for example, carbon dioxide as disclosed in WO04/016277, which components may support an "entourage" effect in the endocannabinoid system.

On dosage, a rat/human conversion factor (×6) suggests a CBD daily dose of at least 600 mg (and optionally between 400 mg and 800 mg) and for THCV at least 1.5 mg (medium) to preferably at least 15 mg (high).

Where a phytocannabinoid extract is to be used, an extract with low or negligible levels of THC and therapeutically effective levels of THCV and/or CBD is desired.

The data described in the Examples above clearly show that although CBD shows some anti-convulsant properties in all of the three models tested, it would appear best in treating generalized or partial seizures. In contrast THCV was only effective in the PTZ-model. This finding suggests that the two cannabinoids may have different mechanisms of action and that the combination may provide for more general treatments. In this regard THCV appears selective for generalized seizures, more particularly tonic-clonic seizures and CBD appears to be most effective in generalized and partial seizures.

REFERENCES

ALGER, B. E. (2006) Not too excited? Thank your endocannabinoids. *Neuron*, 51, 393-5.

AMES F R. (1986) Anticonvulsant effect of cannabidiol. *South African Medical Journal* 69:14.

AVOLI, M., LOUVEL, J., PUMAIN, R. & KOHLING, R. (2005) Cellular and molecular mechanisms of epilepsy in the human brain. *Prog Neurobiol*.

BOSTANCI, M. O. & BAGIRICI, F. (2006) The effects of octanol on penicillin induced epileptiform activity in rats: an in vivo study. *Epilepsy Res*, 71, 188-94.

BRUST, J. C., NG, S. K., HAUSER, A. W. & SUSSER, M. (1992) Marijuana use and the risk of new onset seizures. *Trans Am Clin Climatol Assoc*, 103, 176-81.

CONSROE, P. F., WOOD, G. C. & BUCHSBAUM, H. (1975) Anticonvulsant Nature of Marihuana Smoking. *J. American Medical Association* 234 306-307

CUNHA, J. M., CARLINI, E. A., PEREIRA, A. E., RAMOS, O. L., PIMENTEL, C., GAGLIARDI, R., SANVITO, W. L., LANDER, N. & MECHOULAM, R. (1980) Chronic administration of cannabidiol to healthy volunteers and epileptic patients. *Pharmacology*, 21, 175-85.

DAVIS, J P., & RAMSEY, H. H. (1949) Antiepileptic Action of Marijuana-active Substances. Federation Proceedings 8 284-285

DREIFUSS, F. E., BANCAUD, J., HENRIKSEN, O., RUBIO-DONNADIEU, F. PENRY, J. K. & SEINO, M. (1981) Proposal for revised clinical and electroencephalographic classification of epileptic seizures. *Epilepsia*, 22, 489-501.

FERDINAND, R. F., VAN DER ENDE, J., BONGERS, I., SELTEN, J. P., HUIZINK, A. & VERHULST, F. C. (2005) *Cannabis*—psychosis pathway independent of other types of psychopathology. *Schizophr Res*, 79, 289-95.

FISHER, R. S., VICKREY, B. G., GIBSON, P., HERMANN, B., PENOVICH, P., SCHERER, A. & WALKER, S. (2000) The impact of epilepsy from the patient's perspective I. Descriptions and subjective perceptions. *Epilepsy Res*, 41, 39-51.

GASTAUT, H. (1970) Clinical and Electroencephalographical Classification of Epileptic Seizures. *Epilepsia*, 11, 102-112.

INSTITUTE OF MEDICINE (1999) Marijuana and medicine: Assessing the science base. National Academy Press LUTZ, B. (2004) On-demand activation of the endocannabinoid system in the control of neuronal excitability and epileptiform seizures. *Biochem Pharmacol*, 68, 1691-8.

MACKIE, K. (2006) Cannabinoid receptors as therapeutic targets. *Annu Rev Pharmacol Toxicol,* 46, 101-22.

MCCORMICK, D. A. & CONTRERAS, D. (2001) On the cellular and network bases of epileptic seizures. *Annu Rev Physiol,* 63, 815-46.

MERLIS, J. K. (1970) Proposal for an International Classification of the Epilepsies. *Epilepsia,* 11, 114-119.

NG et al. (1990) Illicit drug use and the risk of new-onset seizures, *American Journal of Epidemiology* 132: 47-57.

OBAY, B. D., TASDEMIR, E., TUMER, C., BILGIN, H. M. & SERMET, A. (2007) Antiepileptic effects of ghrelin on pentylenetetrazole-induced seizures in rats. *Peptides,* 28, 1214-9.

PEREIRA, M. B., FREITAS, R. L., ASSIS, M. A., SILVA, R. F., FONTELES, M. M., FREITAS, R. M. & TAKAHASHI, R. N. (2007) Study pharmacologic of the GABAergic and glutamatergic drugs on seizures and status epilepticus induced by pilocarpine in adult Wistar rats. *Neurosci Lett,* 419, 253-7.

RAUCA, C., WISWEDEL, I., ZERBE, R., KEILHOFF, G. & KRUG, M. (2004) The role of superoxide dismutase and alpha-tocopherol in the development of seizures and kindling induced by pentylenetetrazol—influence of the radical scavenger alpha-phenyl-N-tert-butyl nitrone. *Brain Res,* 1009, 203-12.

SANDER, J. W. (2003) The epidemiology of epilepsy revisited. *Curr Opin Neurol,* 16, 165-70.

SWANN, J. W. (2004) The effects of seizures on the connectivity and circuitry of the developing brain. *Ment Retard Dev Disabil Res Rev,* 10, 96-100.

TREMBLY B. SHERMAN M. (1990) Double-blind clinical study of cannabidiol as a secondary anticonvulsant. *Marijuana '90 International Conference on Cannabis and Cannabinoids.* Kolympari, Crete, Jul. 8-11, 1990.

WINGERCHUK, D. (2004) *Cannabis* for medical purposes: cultivating science, weeding out the fiction. *Lancet,* 364, 315-6

The invention claimed is:

1. A method of treating complex partial seizure comprising administering cannabidiol (CBD) to a patient wherein the CBD is present in an amount which provides a daily dose of at least 400 mg.

2. The method of claim 1, wherein CBD is present in an amount which provides a daily dose of from 400 to 800 mg.

3. The method of claim 1, wherein the CBD is used in combination with tetrahydrocannabivarin (THCV).

4. The method of claim 3, wherein the THCV is present in an amount which provides a daily dose of at least 1.5 mg.

5. The method of claim 4, wherein the THCV is present in an amount which provides a daily dose of at least 15 mg.

6. The method of claim 1, wherein the CBD is present as a plant extract.

7. The method of claim 6, wherein the plant extract comprises less than 5% by weight of tetrahydrocannabinol (THC) as a percentage of any cannabinoids present in the plant extract.

8. The method of claim 7, wherein the plant extract comprises less than 1% by weight of tetrahydrocannabinol (THC) as a percentage of any cannabinoids present in the plant extract.

9. The method of claim 1, wherein the CBD is present as a pure or isolated cannabinoid.

10. The method of claim 3, wherein the CBD in combination with THCV is present as a plant extract.

11. The method of claim 10, wherein the plant extract comprises less than 5% by weight of tetrahydrocannabinol (THC) as a percentage of any cannabinoids present in the plant extract.

12. The method of claim 11, wherein the plant extract comprises less than 1% by weight of tetrahydrocannabinol (THC) as a percentage of any cannabinoids present in the plant extract.

13. The method of claim 3, wherein the CBD in combination with THCV is present as a pure or isolated cannabinoid.

* * * * *